(12) United States Patent
Josel et al.

(10) Patent No.: US 11,267,827 B2
(45) Date of Patent: Mar. 8, 2022

(54) MULTIFUNCTIONALIZED SILICON NANOPARTICLES, PROCESS FOR THEIR PREPARATION AND USES THEREOF IN ELECTROCHEMILUMINESCENCE BASED DETECTION METHODS

(71) Applicant: Roche Diagnostics Operations, Inc., Indianapolis, IN (US)

(72) Inventors: Hans-Peter Josel, Weilheim (DE); Tobias Oelschlaegel, Munich (DE); Giuseppe Prencipe, Penzberg (DE); Luisa De Cola, Strasbourg (FR); Elena Longhi, Atlanta, GA (US); Chien-Wei Hsu, Goeteborg (SE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/284,346

(22) Filed: Feb. 25, 2019

(65) Prior Publication Data
US 2020/0024292 A1    Jan. 23, 2020

Related U.S. Application Data

(63) Continuation of application No. PCT/EP2017/071271, filed on Aug. 24, 2017.

(30) Foreign Application Priority Data

Aug. 25, 2016 (EP) .................................. 16001867

(51) Int. Cl.
*C07F 7/08* (2006.01)
*C09K 11/06* (2006.01)
(Continued)

(52) U.S. Cl.
CPC .............. *C07F 7/081* (2013.01); *C09K 11/06* (2013.01); *B82Y 15/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| 5,147,777 A | 9/1992 | Sutton et al. |
| 5,221,605 A | 6/1993 | Bard et al. |

(Continued)

FOREIGN PATENT DOCUMENTS

| CN | 104822696 A | 8/2015 |
| EP | 0404097 A2 | 12/1990 |

(Continued)

OTHER PUBLICATIONS

Babu, Ethiraju et al., Highly Sensitive Optical Biosensor for Thrombin Based on Structure Switching Aptamer-Luminescent Silica Nanoparticles, Journal of Fluorescence, 2012, pp. 137-146, vol. 23.

(Continued)

*Primary Examiner* — Clinton A Brooks
(74) *Attorney, Agent, or Firm* — Stinson LLP

(57) ABSTRACT

The present disclosure relates to novel multifunctionalized silicon nanoparticles, to processes for their preparation and to compositions comprising the novel multifunctionalized silicon nanoparticles. The disclosure also relates to the use of the novel multifunctionalized silicon nanoparticles in electrochemiluminescence based detection methods and in the in vitro detection of an analyte. In particular, the disclosure relates to methods for measuring an analyte by in vitro methods employing the novel multifunctionalized silicon nanoparticles.

12 Claims, 12 Drawing Sheets

(51) Int. Cl.
*B82Y 15/00* (2011.01)
*B82Y 30/00* (2011.01)
*B82Y 40/00* (2011.01)

(56) References Cited

U.S. PATENT DOCUMENTS

| | | | |
|---|---|---|---|
| 5,532,170 | A | 7/1996 | Buckle et al. |
| 6,316,607 | B1 | 11/2001 | Massey et al. |
| 6,808,939 | B2 | 10/2004 | Sigal et al. |
| 7,115,688 | B1 | 10/2006 | Mirkin et al. |
| 7,521,541 | B2 | 4/2009 | Eigenbrot et al. |
| 8,889,830 | B2 | 11/2014 | Komatsu et al. |
| 9,382,290 | B2 | 7/2016 | Courage et al. |
| 9,499,573 | B2 | 11/2016 | Bergmann et al. |
| 10,130,588 | B2 * | 11/2018 | Stephan ............... A61K 9/5123 |
| 10,399,941 | B2 | 9/2019 | Zhao et al. |
| 2004/0053222 | A1 | 3/2004 | Storhoff et al. |
| 2007/0275383 | A1 | 11/2007 | Vocanson et al. |
| 2009/0317335 | A1 | 12/2009 | Lin et al. |
| 2010/0151485 | A1 | 6/2010 | Rai et al. |
| 2011/0256528 | A1 | 10/2011 | Poetter et al. |
| 2014/0051186 | A1 | 2/2014 | Aizawa et al. |
| 2016/0018404 | A1 | 1/2016 | Iyer et al. |
| 2016/0146826 | A1 | 5/2016 | Zhou et al. |

FOREIGN PATENT DOCUMENTS

| | | |
|---|---|---|
| JP | S62231171 A | 10/1987 |
| JP | H04339808 A | 11/1992 |
| JP | H06505340 A | 6/1994 |
| JP | 2002267671 A | 9/2002 |
| JP | 2002531830 A | 9/2002 |
| JP | 2005532456 A | 10/2005 |
| JP | 2007512522 A | 5/2007 |
| JP | 2008516896 A | 5/2008 |
| JP | 2010010720 A | 1/2010 |
| JP | 2012509070 A | 4/2012 |
| JP | 2014514330 A | 6/2014 |
| JP | 2015524796 A | 8/2015 |
| JP | 2016105066 A | 6/2016 |
| JP | 2016520287 A | 7/2016 |
| WO | 1993/001161 A1 | 1/1993 |
| WO | 2003/002974 A2 | 1/2003 |
| WO | 2012/107419 A1 | 8/2012 |
| WO | 2012/107420 A1 | 8/2012 |
| WO | 2012117688 A1 | 9/2012 |
| WO | 2012147774 A1 | 11/2012 |
| WO | 2013/087734 A2 | 6/2013 |
| WO | 2014/019707 A2 | 2/2014 |
| WO | 2014/019708 A1 | 2/2014 |
| WO | 2014/019709 A2 | 2/2014 |
| WO | 2014/019710 A1 | 2/2014 |
| WO | 2014/019711 A1 | 2/2014 |
| WO | 2016/075670 A1 | 5/2016 |

OTHER PUBLICATIONS

Holliger, Philipp et al., "Diabodies": Small bivalent and bispecific antibody fragments, Proceedings of the National Academy of Sciences USA, 1993, pp. 6444-6448, vol. 90.

Hudson, Peter J. and Souriau, Christelle, Engineered antibodies, Nature Medicine, 2003, pp. 129-134, vol. 9, No. 1.

International Search Report dated Nov. 2, 2017, in Application No. PCT/EP2017/071271, 4 pp.

Kim, Yang-Rae et al., Immunosensor Based on Electrogenerated Chemiluminescence Using Ru (bpy)32+—Doped Silica Nanoparticles and Calix [4]crown-5 Self-Assembled Monolayers, Electroanalysis, 2013, pp. 1056-1063, vol. 25, No. 4.

Liang, Wenbin et al., Ultrasensitive Cytosensor Based on Self-Enhanced Electrochemiluminescent Ruthenium-Silica Composite Nanoparticles for Efficient Drug Screening with Cell Apoptosis Monitoring, Analytical Chemistry, 2015, p. 12363-12371, vol. 87.

Plückthun, A., Antibodies from *Escherichia coli*, The Pharmacology of Monoclonal Antibodies, 1994, pp. 269-315, vol. 113, Chapter 11, Springer-Verlag, New York.

Rosso-Vasic, Milena et al., Alkyl-Functionalized Oxide-Free Silicon Nanoparticles: Synthesis and Optical Properties, Small, 2008, pp. 1835-1841, vol. 4, No. 10.

Rosso-Vasic, Milena et al., Amine-terminated silicon nanoparticles: synthesis, optical properties and their use in bioimaging, Journal of Materials Chemistry, 2009, pp. 5926-5933, vol. 19.

Wang, Jing et al., Quantum Dot-Based Near-Infrared Electrochemiluminescent Immunosensor with Gold Nanoparticle-Graphene Nanosheet Hybrids and Silica Nanospheres Double-Assisted Signal Amplification, Analytical Chemistry, 2012, pp. 4893-4899, vol. 84.

Warner, Jamie H. et al., Water-Soluble Photoluminescent Silicon Quantum Dots, Angewandte Chemic, 2005, pp. 4626-4630, vol. 117.

Zhang, Yan et al., Ultrasensitive electrochemiluminescent immunosensor based on dual signal amplification strategy of gold nanoparticles-dotted graphene composites and CdTe quantum dots coated silica nanoparticles, Analytical and Bioanalytical Chemistry, 2013, pp. 4921-4929, vol. 405.

Zhong, Yiling et al., Large-Scale Aqueous Synthesis of Fluorescent and Biocompatible Silicon Nanoparticles and Their Use as Highly Photostable Biological Probes, Journal of the American Chemical Society, 2013, pp. 8350-8356, vol. 135.

Tan, Jie et al., Image-Contrast Technology Based on the Electrochemiluminescence of Porous Silicon and Its Application in Fingerprint Visualization, Angewandte Chemie International Edition, 2014, pp. 9822-9826, vol. 53.

Bae et al., Electrochemistry and electrogenerated chemiluminescence of films of silicon nanoparticles in aqueous solution; Nanotechnology; 2006, 7-pages.

Rosso-Vasic et al., Synthesis and Photophysics of Funtionalized Silicon Nanoparticles; 18-pages.

Shao et al., Stretch-Stowage-Growth Strategy to Fbricate Tunable Triple-Amplified Electrochemiluminescence Immunosensor for Ultrasensitive Detection of Pseudorabies Virus Antibody; Analytical Chemistry; 9-pages.

* cited by examiner

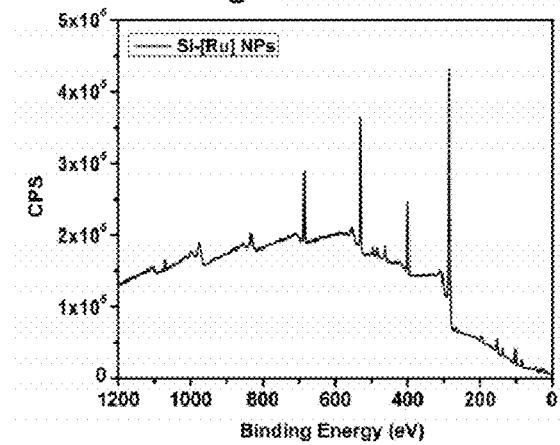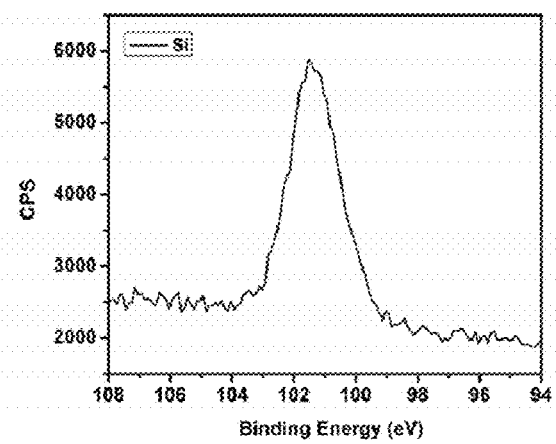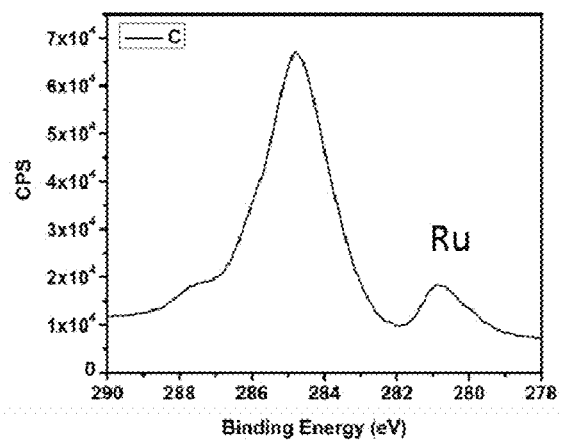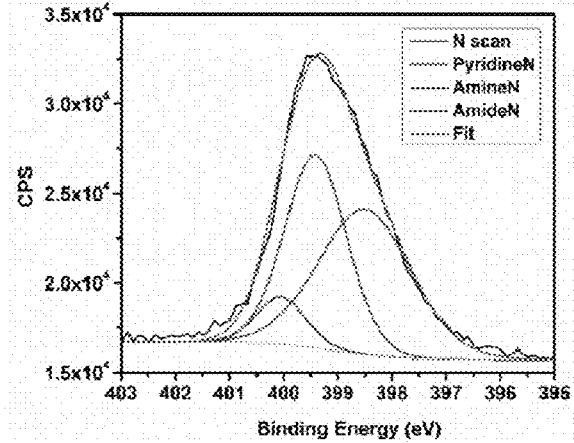

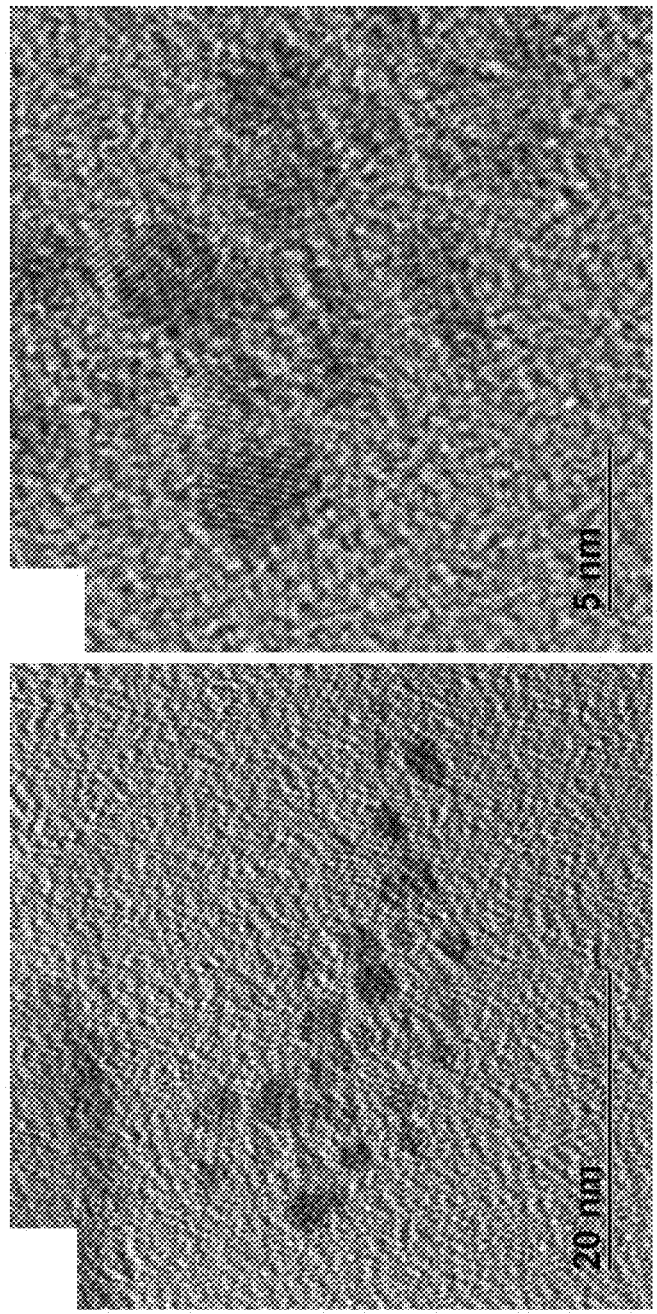

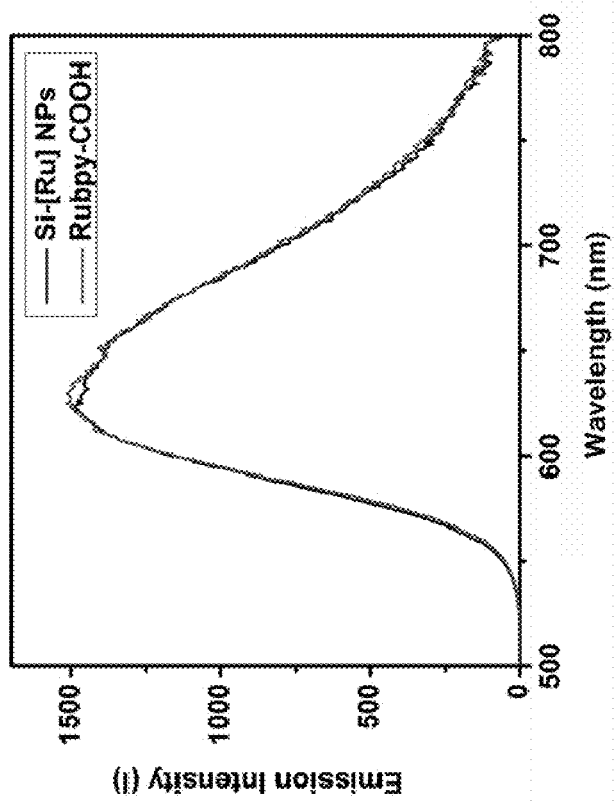
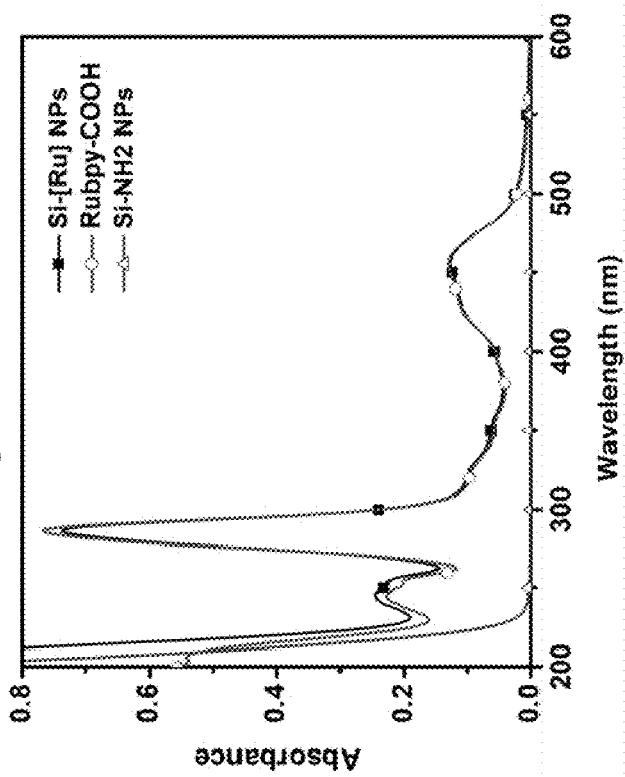

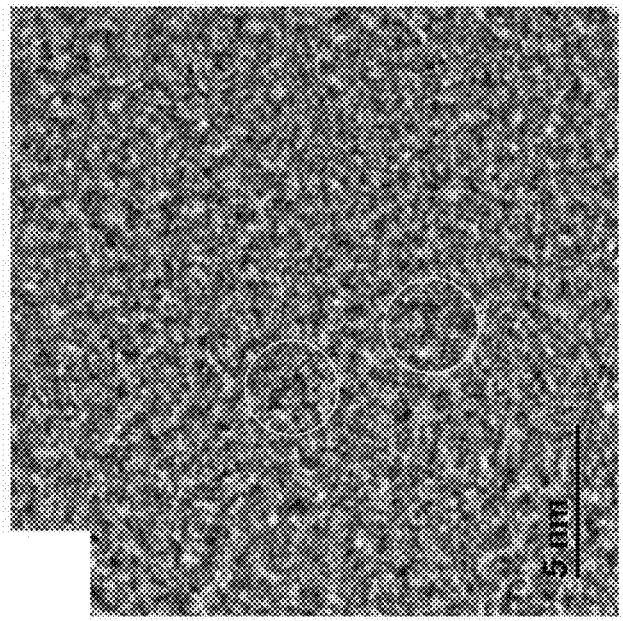
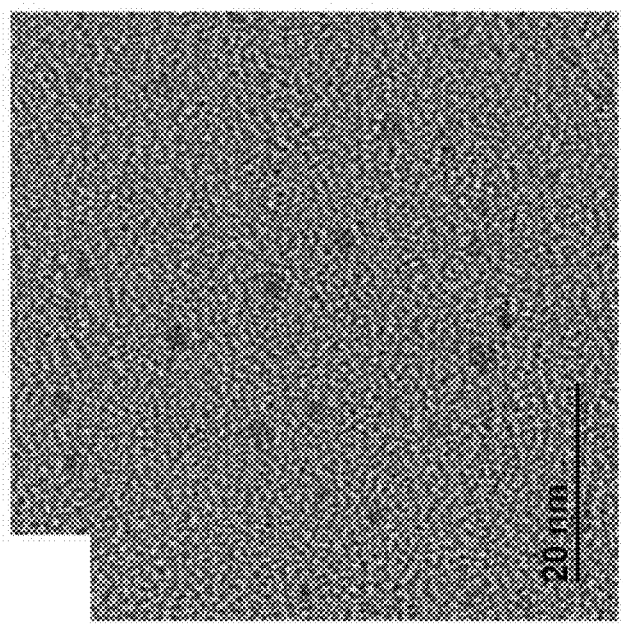

MULTIFUNCTIONALIZED SILICON NANOPARTICLES, PROCESS FOR THEIR PREPARATION AND USES THEREOF IN ELECTROCHEMILUMINESCENCE BASED DETECTION METHODS

CROSS-REFERENCE TO RELATED APPLICATIONS

This application is a continuation of International Application No. PCT/EP2017/071271 filed Aug. 24, 2017, which claims priority to European Application 16001867.7 filed Aug. 25, 2016, the disclosures of which are hereby incorporated by reference in their entirety.

FIELD OF THE INVENTION

The present invention relates to novel multifunctionalized silicon nanoparticles, to processes for their preparation and to compositions comprising the novel multifunctionalized silicon nanoparticles. The invention also relates to the use of the novel multifunctionalized silicon nanoparticles in electrochemiluminescence based detection methods and in the in vitro detection of an analyte. In particular, the invention relates to methods for measuring an analyte by in vitro methods employing the novel multifunctionalized silicon nanoparticles.

BACKGROUND OF THE INVENTION

Silicon nanoparticles have a high specific surface area, providing for high capacity for drug loading. Their high biocompatibility and low toxicity in vivo makes silicon nanoparticles attractive materials, especially for drug/compound delivery into cells.

Y.-R. Kim et al. (Y.-R. Kim et al., Electroanalysis 2013, 25(4), 1056-1063), describe an electrogenerated chemiluminescence (ECL)-based immunosensor for the detection of immunoglobulin G (IgG) based on $Ru(bpy)_3^{2+}$-doped silica nanoparticles and calix[4]crown-5 self-assembled monolayers.

WO 2013/087734 A2 describes silicon nanoparticles, which are functionalized with radioactive metal complexes comprising therapeutically relevant radionuclides and their use in radionuclide therapy.

Electrogenerated chemiluminescence (also called electrochemiluminescence and abbreviated ECL) is the process whereby oxidized co-reactants generated at electrodes undergo high-energy electron-transfer reactions to form excited states of metal complexes that emit light. The first detailed ECL studies were described by Hercules and Bard et al. in the mid-1960s. After about 50 years of study, ECL has now become a very powerful analytical technique and is widely used in the areas of, for example, immunoassay, food and water testing, and biowarfare agent detection.

In practice, most ECL-based immunoassays involve the use of electrochemiluminescent compounds as labels. The presence of a labeled substance or the participation of a labeled substance in a binding reaction is determined via detection of electrochemiluminescence from the ECL label.

There is always a high need for more sensitive detection methods in immuno assays. This is also true for electrochemiluminescence based detection methods. It was now surprisingly found that it is possible to provide novel multifunctionalized silicon nanoparticles for use in ECL-based immunoassays, and that unexpectedly such multifunctionalized silicon nanoparticles can be used with great advantages in these assays.

SUMMARY OF THE INVENTION

The present invention, in one aspect, relates to multifunctionalized silicon nanoparticles comprising
(a) a silicon core of a size of from 1 nm to 10 nm,
(b) amine-terminated $C_3$-$C_{18}$ aminoalkyl groups, amine-terminated 3-(2-amino-ethoxy)-propyl groups, amine-terminated 3-[2-(2-amino-ethoxy)-ethoxy]-propyl groups or amine-terminated 2-(4-amino-methyl-phenyl)-ethyl groups, wherein the groups are covalently bound to the silicon core,
(c) from 1 to 10 affinity binding agents covalently bound to amine-terminated $C_3$-$C_{18}$ aminoalkyl groups, to amine-terminated 3-(2-amino-ethoxy)-propyl groups, to amine-terminated 3-[2-(2-amino-ethoxy)-ethoxy]-propyl groups or to amine-terminated 2-(4-amino-methyl-phenyl)-ethyl groups, preferably via a linker, and
(d) from 1 to 100 electrochemiluminescent compounds covalently bound to amine-terminated $C_3$-$C_{18}$ aminoalkyl groups, to amine-terminated 3-(2-amino-ethoxy)-propyl groups, to amine-terminated 3-[2-(2-amino-ethoxy)-ethoxy]-propyl groups or to amine-terminated 2-(4-amino-methyl-phenyl)-ethyl groups, preferably via a linker.

In one embodiment, the multifunctionalized silicon nanoparticles correspond to Formula (I)

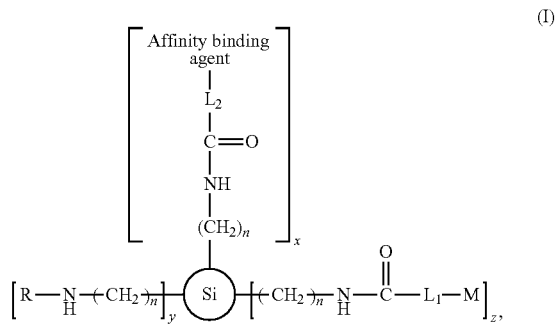

wherein
n is an integer from 3 to 18,
x is an integer from 1 to 10,
y is at least 1,
z is an integer from 1 to 100,
$L_1$ is a linker,
$L_2$ is a linker,
wherein $L_1$ and $L_2$ are identical or different,
Si is a silicon core having a size of from 1 nm to 10 nm,
R is H, —CO-L2 with one reactive group, —CO-deactivated $L_2$, wherein $L_2$ is as defined above, or a residue resulting from a surface modification reagent, and
M is an electrochemiluminescent metal complex, or a salt thereof.

In another embodiment, in the multifunctionalized silicon nanoparticles as defined above, the affinity binding agent is selected from the group consisting of an analyte, a protein, an antibody, biotin, a biotin analogue, avidin, streptavidin, a sugar, lectin, an enzyme, a polypeptide, a nucleic acid, a nucleic acid analogue, a complementary nucleic acid, a nucleotide, a polynucleotide, a peptide nucleic acid (PNA), a polysaccharide, a metal-ion sequestering agent, a receptor agonist, and a receptor antagonist. In a preferred embodiment, the affinity binding agent is a nucleic acid, a complementary nucleic acid, an antigen or an antibody, or an analyte.

In another embodiment, in the multifunctionalized silicon nanoparticles as defined above, the affinity binding agent is a partner or member of an affinity binding pair.

In another embodiment, in the multifunctionalized silicon nanoparticles as defined above, the affinity binding agent is a member of a binding pair selected from nucleic acid and complementary nucleic acid, or antigen and antibody.

In another embodiment, in the multifunctionalized silicon nanoparticles as defined above, n is 3, 6 or 11, preferably n is 3.

In another embodiment, in the multifunctionalized silicon nanoparticles as defined above, x is an integer from 1 to 5, from 1 to 4, from 1 to 3, is 1 or 2, or 1.

In another embodiment, in the multifunctionalized silicon nanoparticles as defined above, y is an integer from 1 to 1000, preferably y is an integer from 1 to 500.

In another embodiment, in the multifunctionalized silicon nanoparticles as defined above, z is an integer from 1 to 90, e.g. from 20 to 90, from 30 to 90, from 40 to 90, from 50 to 90, from 60 to 90, from 70 to 80, from 1 to 80, from 1 to 70, from 1 to 60, from 1 to 50 or from 1 to 40. In a preferred embodiment, z is an integer from 50 to 100. In a particularly preferred embodiment, z is an integer from 50 to 70.

In another embodiment, in the multifunctionalized silicon nanoparticles as defined above, $L_1$ has as a backbone a straight- or branched-chain unsubstituted or substituted $C_1$-$C_{20}$ alkyl chain, $C_1$-$C_{20}$ alkenyl chain or a 1 to 20 atom chain consisting of carbon atoms, substituted carbon atoms and/or one or more atoms selected from O, N and S, or a chain as described before with the backbone containing one or more cyclic or heterocyclic aromatic or non-aromatic ring systems.

In another embodiment, in the multifunctionalized silicon nanoparticles as defined above, $L_2$ is a linker that is formed by reaction of a heterobifunctional crosslinker, which is for example heterobifunctional for binding to sulfhydryl groups and to amino groups, respectively.

Any combinations of any embodiments of the multifunctionalized silicon nanoparticles as defined herein are considered to be within the scope of the invention.

In another aspect, the present invention relates to the use of multifunctionalized silicon nanoparticles as defined above in an electrochemiluminescence based detection method.

In another aspect, the present invention relates to the use of multifunctionalized silicon nanoparticles as defined above for performing an electrochemiluminescence reaction in an aqueous solution.

In another aspect, the present invention relates to the use of multifunctionalized silicon nanoparticles as defined above in the in vitro detection of an analyte.

In another aspect, the present invention relates to a composition comprising multifunctionalized silicon nanoparticles as defined above.

In another aspect, the present invention relates to a method for measuring an analyte by an in vitro method, the method comprising the steps of:
(a) providing a sample suspected or known to comprise the analyte,
(b) contacting said sample with multifunctionalized silicon nanoparticles as defined above, under conditions appropriate for the formation of a complex of the analyte with the multifunctionalized silicon nanoparticles to obtain an analyte-multifunctionalized silicon nanoparticle complex, and
(c) measuring the analyte-multifunctionalized silicon nanoparticle complex formed in step (b) and thereby obtaining a measure of the analyte.

In another aspect, the present invention relates to a method for measuring an analyte by an in vitro method, the method comprising the steps of:
(a) providing a sample suspected or known to comprise the analyte,
(b) contacting said sample with multifunctionalized silicon nanoparticles as defined above, wherein said nanoparticles comprise the analyte, with an analyte-specific affinity binding agent under conditions appropriate for the formation of a complex of multifunctionalized silicon nanoparticles and analyte-specific affinity binding agent to obtain an analyte-specific affinity binding agent-multifunctionalized silicon nanoparticle complex, and
(c) measuring the analyte-specific affinity binding agent-multifunctionalized silicon nanoparticle complex formed in step (b) and thereby obtaining a measure of the analyte.

BRIEF DESCRIPTION OF THE FIGURES

FIG. 1A shows a survey scan of XPS spectra of Si—[Ru] nanoparticles.

FIG. 1B shows an SI scan of XPS spectra of Si—[Ru] nanoparticles.

FIG. 1C shows a C scan of XPS spectra of Si—[Ru] nanoparticles.

FIG. 1D shows an N scan with deconvolution of XPS spectra of Si—[Ru] nanoparticles.

FIG. 2A shows TEM images of Si—[Ru] nanoparticles at 20 nm.

FIG. 2B shows TEM images of Si—[Ru] nanoparticles at 5 nm.

FIG. 3A shows the UV-Vis absorption spectra of Si—NH2 nanoparticles, Si—[Ru] nanoparticles and Rubpy in aqueous solution.

FIG. 3B shows emission spectra of Si—[Ru] nanoparticles and Rubpy-COOH in water solution at $\lambda_{ex}=375$ nm. The concentration of Rubpy is $10^{-5}$ M.

FIG. 7 shows XPS spectra of Si—[Ir] nanoparticles.

FIG. 8A shows a TEM image of Si—[Ir] nanoparticles at 20 nm. The concentration of Ir complex is $10^{-5}$ M.

FIG. 8B shows a TEM image of Si—[Ir] nanoparticles at 5 nm. The concentration of Ir complex is $10^{-5}$ M.

DETAILED DESCRIPTION OF THE INVENTION

Novel Multifunctional Silicon Nanoparticles

Figure 4:
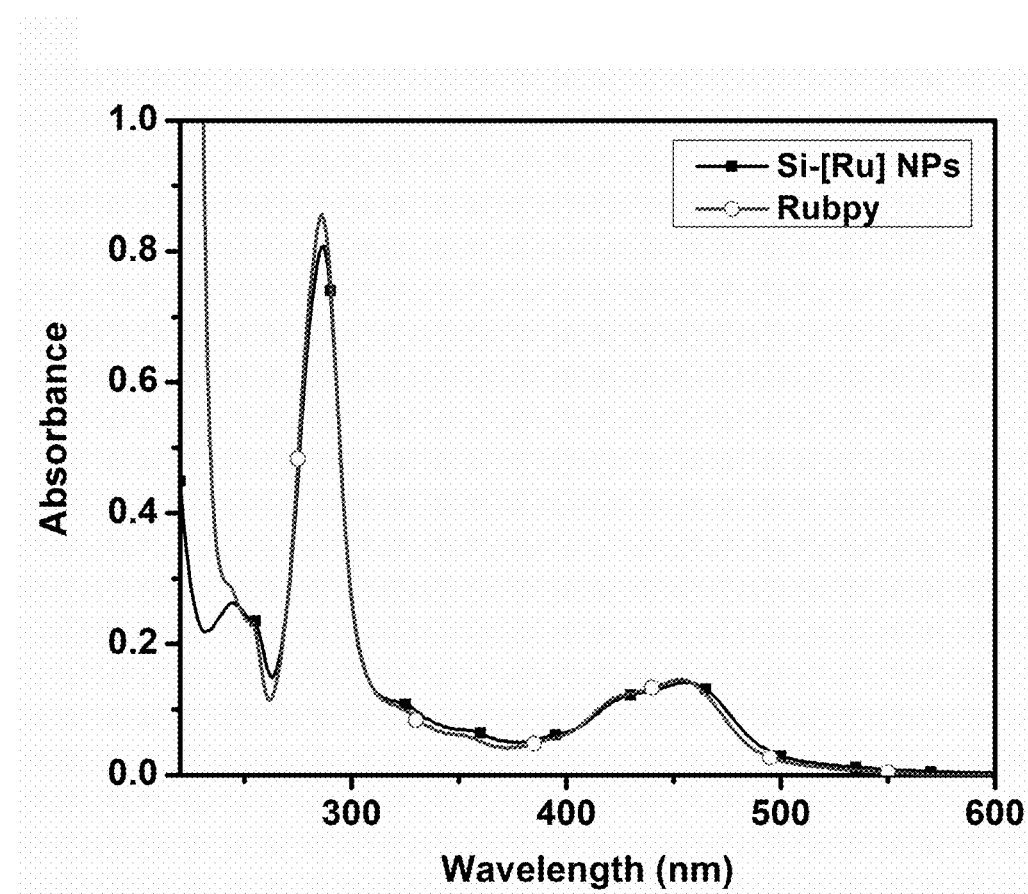
FIG. 4 shows the UV-Vis absorption spectra of Si-[Ru] nanoparticles and Rubpy in ProCell solution. The concentration of Rubpy is $10^{-5}$ M.

As indicated above, there is a need for multifunctionalized silicon nanoparticles which are suitable for use in electrochemiluminescence based detection methods and in the in vitro detection of an analyte, in particular in ECL-based immunoassays such as ECL based sandwich immunoassays. In particular, the need exists for silicon nanoparticles for ECL-based immunoassays, which allow tailoring the physical and chemical properties of the silicon nanoparticles by optimizing the size and surface functionalization of the nanoparticles.

A problem solved by the present invention was therefore to provide multifunctionalized silicon nanoparticles having the above-mentioned desired characteristics.

In one aspect, the present invention provides novel multifunctionalized silicon nanoparticles comprising
(a) a silicon core of a size of from 1 nm to 10 nm,
(b) amine-terminated $C_3$-$C_{18}$ aminoalkyl groups, amine-terminated 3-(2-amino-ethoxy)-propyl groups, amine-terminated 3-[2-(2-amino-ethoxy)-ethoxy]-propyl groups or amine-terminated 2-(4-amino-methyl-phenyl)-ethyl groups, wherein the groups are covalently bound to the silicon core,
(c) from 1 to 10 affinity binding agents covalently bound to amine-terminated $C_3$-$C_{18}$ aminoalkyl groups, to amine-terminated 3-(2-amino-ethoxy)-propyl groups, to amine-terminated 3-[2-(2-amino-ethoxy)-ethoxy]-propyl groups or to amine-terminated 2-(4-amino-methyl-phenyl)-ethyl groups, preferably via a linker, and
(d) from 1 to 100 electrochemiluminescent compounds covalently bound to amine-terminated $C_3$-$C_{18}$ aminoalkyl groups, to amine-terminated 3-(2-amino-ethoxy)- propyl groups, to amine-terminated 3-[2-(2-amino-ethoxy)-ethoxy]-propyl groups or to 2-(4-amino-methyl-phenyl)-ethyl groups, preferably via a linker.

The silicon core has a size of from 1 nm to 10 nm and comprises a plurality of silicon atoms. In one embodiment the size of the silicon core ranges from 1 nm to 9 nm, e.g. from 1 nm to 8 nm, from 1.5 nm to 7 nm, from 2 nm to 6 nm, from 2 nm to 5nm.

The amine-terminated $C_3$-$C_{18}$ aminoalkyl groups, amine-terminated 3-(2-amino-ethoxy)-propyl groups, amine-terminated 3-[2-(2-amino-ethoxy)-ethoxy]-propyl groups and amine-terminated 2-(4-amino-methyl-phenyl)-ethyl groups, are covalently bound to the silicon core by means of an Si—C bond.

As used herein, including the accompanying claims, the terms, which are collectively used, have the following meanings.

As used herein, the term "multifunctionalized silicon nanoparticles" means that at least two different kinds of functional compounds are bound to the surface of the silicon core of the silicon nanoparticles. In one embodiment, the functional compounds are bound to the silicon core via a linker to the amine-terminated $C_3$-$C_{18}$ aminoalkyl groups, amine-terminated 3-(2-amino-ethoxy)-propyl groups, amine-terminated 3-[2-(2-amino-ethoxy)-ethoxy]-propyl groups or amine-terminated 2-(4-amino-methyl-phenyl)-ethyl groups.

As used herein, the term "functional compound" means any compound that is needed for a specific application, for example for targeting a specific kind of tissue or cell, or for allowing detection in an assay. Examples include but are not limited to affinity binding agents, any labels such as electrochemiluminescent compounds and fluorescent compounds for use in assays for measuring an analyte of interest. In one embodiment at least one functional compound comprised in the multifunctionalized silicon nanoparticles is an affinity binding agent and at least one compound comprised in the multifunctionalized silicon nanoparticles is an electrochemiluminescent compound.

The term "linker" as used herein, has the meaning known to a person skilled in the art and relates to a molecule or groups of molecules, which are used to link two or more molecules. Linkers are characterized by having two or more chemically orthogonal functionalities on a flexible or rigid scaffold. A covalent bond is not a linker in the sense of the present invention.

As used herein, the term "$C_3$-$C_{18}$ aminoalkyl" alone or in combination means an $H_2N$-R'-group, wherein R' is $C_3$-$C_{18}$ alkyl and is a straight-chain or branched alkyl group with 3 to 18 carbon atoms, preferably a straight- or branched-chain alkyl group with 3, 6 or 11 carbon atoms and particularly preferred a straight-chain alkyl group with 3 carbon atoms. Examples of straight-chain $C_3$-$C_{18}$ aminoalkyl groups are aminopropyl, aminobutyl, aminohexyl, and aminoundecyl, preferably aminopropyl.

As used herein, the term "affinity binding agent" means a molecule capable of molecular binding to another molecule (target molecule or target) due to attractive interaction between these molecules that results in a stable association in which the molecules are close to each other. The result of molecular binding is the formation of a molecular complex. The attractive bonding between the components of a complex is normally weaker than in a covalent bond. In the present case, the binding agent is an affinity binding agent, which means that it is capable of forming an affinity complex between the affinity binding agent and its target. Such a complex is stable under the respective conditions, e.g. in aqueous medium under standard conditions. Molecules that can participate in molecular binding include, but are not limited to, proteins, nucleic acids, carbohydrates, lipids, and small organic molecules such as drugs. Hence the types of complexes that form as a result of molecular binding include but are not limited to the following affinity binding agent—target molecule complexes: protein—protein, protein—DNA, protein—hormone, protein—drug, antigen—antibody, receptor—ligand, biotin—avidin or streptavidin, nucleic acid—complementary nucleic acid or receptor—receptor (ant)agonist.

Examples of affinity binding agents include, but are not limited to analytes, antigens, proteins, antibodies, biotin, biotin analogues, avidin, streptavidin, sugars, lectin, enzymes, polypeptides, nucleic acids, nucleic acid analogues, complementary nucleic acids, nucleotides, polynucleotides, peptide nucleic acids (PNA), polysaccharides, metal-ion sequestering agents, receptor agonists or a receptor antagonist. For example, the affinity binding agent can be one partner of a specific binding pair, wherein the other partner of said binding pair is associated with or is the target on a cell surface or an intracellular structure.

An affinity binding agent has at least an affinity of $10^7$ L/mol to its target, e.g. one member of a specific binding pair, like an antibody, to the other member of the specific binding pair, like its antigen. An affinity binding agent preferably has an affinity of $10^8$ L/mol or even more preferred of $10^9$ L/mol for its target.

As used herein, the term "analyte" means any inorganic or organic molecule, including any biological substance of interest. Examples of suitable biological substances that represent an analyte in the sense of the present invention are cells, viruses, subcellular particles, proteins, lipoproteins, glycoproteins, peptides, polypeptides, nucleic acids, oligosaccharides, polysaccharides, lipopoly-saccharides, cellular metabolites, haptens, hormones, pharmacological substances, alkaloids, steroids, vitamins, amino acids and sugars.

The analyte may be selected from the group consisting of a polypeptide, a carbohydrate, and an inorganic or organic drug molecule.

A polypeptide or protein is a molecule that is essentially composed of amino acids and that has at least two amino acids linked by peptidic linkage. In case the analyte of interest to be investigated in a method disclosed here, the polypeptide preferably will consist of at least 5, 6, 7, 8, 9, 10, 12, 15, 20, 25, and 30 to up to about 10,000 amino acids. Preferably the polypeptide will contain from 5 to 2,000, also preferred from 10 to 1,000 amino acids.

In case the analyte is a nucleic acid, these nucleic acids preferably are naturally occurring DNA or RNA oligonucleotides.

Biotin analogues are aminobiotin, iminobiotin or desthiobiotin.

The term "oligonucleotide" or "nucleic acid" as used herein, generally refers to short, generally single stranded, polynucleotides that comprise at least 8 nucleotides and at most about 1000 nucleotides. In a preferred embodiment an oligonucleotide will have a length of at least 9, 10, 11, 12, 15, 18, 21, 24, 27 or 30 nucleotides. In a preferred embodiment an oligonucleotide will have a length of no more than 200, 150, 100, 90, 80, 70, 60, 50, 45, 40, 35 or 30 nucleotides.

The term oligonucleotide is to be understood broadly and includes DNA and RNA as well as analogues and modifications thereof.

A nucleic acid analogue may for example contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases are: 5-substituted pyrimidines like 5 methyl dC, aminoallyl dU or dC, 5-(aminoethyl-3-acrylimido)-dU, 5-propynyl-dU or -dC, 5 halogenated -dU or -dC; N substituted pyrimidines like N4-ethyl-dC; N substituted purines like N6-ethyl-dA, N2-ethyl-dG; 8 substituted purines like 8-[6-amino)-hex-1-yl]-8-amino-dG or -dA, 8 halogenated dA or dG, 8-alkyl dG or dA; and 2 substituted dA like 2 amino dA.

A nucleic acid analogue may contain a nucleotide or a nucleoside analogue. I.e. the naturally occurring nucleobases can be exchanged by using nucleobase analogs like 5-nitroindol-d-riboside; 3-nitro-pyrrole-d-riboside, deoxyinosine (dI), deoxyxanthosine (dX); 7 deaza -dG, -dA, -dI or -dX; 7-deaza-8-aza -dG, -dA, -dI or -dX; 8-aza -dA, -dG, -dI or -dX; d-Formycin; pseudo dU; pseudo iso dC; 4 thio dT; 6 thio dG; 2 thio dT; iso dG; 5-methyl-iso-dC; N8-linked 8-aza-7-deaza-dA; 5,6-dihydro-5-aza-dC; and etheno-dA or pyrrolo-dC. As obvious to the skilled person, the nucleobase in the complementary strand has to be selected in such manner that duplex formation is specific. If, for example, 5-methyl-iso-dC is used in one strand (e.g. (a)) iso dG has to be in the complementary strand (e.g. (a')).

In a nucleic acid analog the oligonucleotide backbone may be modified to contain substituted sugar residues, sugar analogs, modifications in the internucleoside phosphate moiety, and/or be a PNA.

An oligonucleotide may for example contain a nucleotide with a substituted deoxy ribose like 2'-methoxy, 2'-fluoro, 2'-methylseleno, 2'-allyloxy, 4'-methyl dN (wherein N is a nucleobase, e.g., A, G, C, T or U).

Sugar analogs are for example xylose; 2',4' bridged ribose like (2'-O, 4'-C methylene)-(oligomer known as LNA) or (2'-O, 4'-C ethylene)- (oligomer known as ENA); L-ribose, L-d-ribose, hexitol (oligomer known as HNA); cyclohexenyl (oligomer known as CeNA); altritol (oligomer known as ANA); a tricyclic ribose analog where C3' and C5' atoms are connected by an ethylene bridge that is fused to a cyclopropane ring (oligomer known as tricycloDNA); glycerin (oligomer known as GNA); glucopyranose (oligomer known as Homo DNA); carbaribose (with a cyclopentane instead of a tetrahydrofuran subunit); hydroxymethyl-morpholine (oligomers known as morpholino DNA).

A great number of modifications of the internucleosidic phosphate moiety are also known not to interfere with hybridization properties and such backbone modifications can also be combined with substituted nucleotides or nucleotide analogs. Examples are phosphorothioate, phosphorodithioate, phosphoramidate and methylphosphonate oligonucleotides.

PNA (having a backbone without phosphate and d-ribose) can also be used as a DNA analog.

The above mentioned modified nucleotides, nucleotide analogs as well as oligonucleotide backbone modifications can be combined as desired in an oligonucleotide in the sense of the present invention.

In one embodiment, the analyte comprised in multifunctionalized silicon nanoparticles as defined above as an affinity binding agent is a low molecular weight analyte, i.e. an analyte having a molecular weight of 2000 Dalton or less. Preferred analytes comprised in such multifunctionalized silicon nanoparticles are diagnostically relevant hormones or/and metabolites among others. Diagnostically relevant hormones or metabolites include folate, especially the so-called total folate as comprised in both the blood plasma and in the red blood cells, steroids like estradiol, estrone, progesterone, 17-hydroxyprogesterone, cortisol, testosterone, androstendione, and hormones like 25-hydroxy vitamin D3.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, MD (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (K) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab∝)2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Plueckthun, In: The Pharmacology of Monoclonal Antibodies, Vol. 113, Rosenburg and Moore (eds.), Springer-Verlag, New York (1994) pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0 404 097; WO 1993/01161; Hudson, P. J. et al., Nat. Med. 9 (2003) 129-134; and Holliger, P. et al., PNAS USA 90 (1993) 6444-6448. Triabodies and tetrabodies are also described in Hudson, P. J. et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, or to introduce reactive groups like cysteins at defined positions etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

As used herein the term "electrochemiluminescent compounds" means any electrochemiluminescent compound, which can be covalently bound, if appropriate via a linker, to amine-terminated $C_3$-$C_{18}$ aminoalkyl groups, to amine-terminated 3-(2-amino-ethoxy)-propyl groups, to amine-terminated 3-[2-(2-amino-ethoxy)-ethoxy]-propyl groups or to 2-(4-amino-methyl-phenyl)-ethyl groups. Examples of electrochemiluminescent (ECL) compounds include positively charged ECL metal complexes, negatively charged ECL metal complexes and electronically neutral ECL metal complexes.

In one embodiment, the multifunctionalized silicon nanoparticles of the present invention correspond to Formula (I)

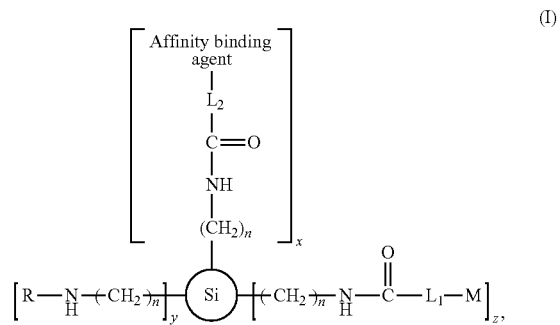

wherein
n is an integer from 3 to 18,
x is an integer from 1 to 10,
y is at least 1,
z is an integer from 1 to 100,
$L_1$ is a linker,
$L_2$ is a linker,
wherein $L_1$ and $L_2$ are identical or different,
Si is a silicon core having a size of from 1 nm to 10 nm
R is H, —CO-$L_2$ with one reactive group, —CO-deactivated $L_2$, wherein $L_2$ is as defined above, or a residue resulting from a surface modification reagent, and
M is an electrochemiluminescent metal complex, or a salt thereof.

In one embodiment, in the multifunctionalized silicon nanoparticles as defined above, the affinity binding agent is selected from the group consisting of an analyte, a protein, an antibody, biotin, a biotin analogue, an avidin, a streptavidin, a sugar, a lectin, an enzyme, a polypeptide, a nucleic acid, a nucleic acid analogue, a complementary nucleic acid, a nucleotide, a polynucleotide, a peptide nucleic acid (PNA), a polysaccharide, a metal-ion sequestering agent, a receptor agonist, and a receptor antagonist. In a preferred embodiment, the affinity binding agent is a nucleic acid, a complementary nucleic acid, an antigen, an antibody, or an analyte.

In another embodiment, the affinity binding agent is a low molecular weight analyte or a derivative thereof, preferably an analyte having a molecular weight of 2000 Dalton or less. Preferred analytes comprised in multifunctionalized silicon nanoparticles of the invention are physiologically/diagnostically relevant hormones and metabolites as defined herein.

As used herein, the term "derivative of a low molecular analyte" means any derivative of the analyte having binding properties, which are comparable to the binding properties of the analyte in a sample.

In another embodiment, in the multifunctionalized silicon nanoparticles as defined above, the affinity binding agent is a partner or member of an affinity binding pair.

In another embodiment, in the multifunctionalized silicon nanoparticles as defined above, the affinity binding agent is a member of a binding pair selected from nucleic acid and complementary nucleic acid, or antigen and antibody.

In another embodiment, in the multifunctionalized silicon nanoparticles as defined above, n is an integer from 3 to 17, e.g. from 3 to 16, from 1 to 15, from 1 to 14, from 3 to 12, or from 3 to 11; preferably, n is 3, 6 or 11. In a particular preferred embodiment n is 3.

In another embodiment, in the multifunctionalized silicon nanoparticles as defined above, x is an integer from 1 to 5, e.g. from 1 to 4, from 1 to 3, 1 or 2, or 1. In a particular preferred embodiment x is 1.

In another embodiment, in the multifunctionalized silicon nanoparticles as defined above, y is an integer from 1 to 1000, e.g. from 1 to 900, from 1 to 800, from 1 to 700, from 1 to 600 or from 1 to 500. In a particular preferred embodiment y is an integer from 1 to 500.

In another embodiment, in the multifunctionalized silicon nanoparticles as defined above, z is an integer from 1 to 90, e.g. from 20 to 90, from 30 to 90, from 40 to 90, from 50 to 90, from 60 to 90, from 70 to 80, from 1 to 80, from 1 to 70, from 1 to 60, from 1 to 50 or from 1 to 40. In a preferred embodiment, z is an integer from 50 to 100. In a particularly preferred embodiment, z is an integer from 50 to 70.

In another embodiment, in the multifunctionalized silicon nanoparticles as defined above, $L_1$ has as a backbone a straight-chain or branched-chain unsubstituted or substituted $C_1$-$C_{20}$ alkyl chain, $C_1$-$C_{20}$ alkenyl chain, or a 1 to 20 atom chain consisting of carbon atoms, substituted carbon atoms and/or one or more atoms selected from O, N and S, or a chain as described before with the backbone containing one or more cyclic or heterocyclic aromatic or non-aromatic ring systems.

As used herein, the term "alkyl" alone or in combination means a straight-chain or branched alkyl group with 1 to 20 carbon atoms, preferably a straight- or branched-chain alkyl group with 1 to 10 carbon atoms and particularly preferred a straight- or branched-chain alkyl group with 1 to 6 carbon atoms; or a heteroalkyl chain with 1 to 20 atoms, preferably with 1 to 10 atoms, comprising 1 to 4 heteroatoms selected from O, N, P, and S. Examples of straight-chain and branched groups include, but are not limited to, methyl, ethyl, propyl, isopropyl, butyl, isobutyl, tert.-butyl, the isomeric pentyls, the isomeric hexyls, the isomeric heptyls, the isomeric octyls, preferably methyl and ethyl and most preferred methyl.

As used herein, the term "alkenyl" alone or in combination means a straight-chain or branched-chain hydrocarbon residue comprising an olefinic bond and 2 to 20, preferably 2 to 10, particularly preferred 2 to 6 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

As used herein, the term "$C_1$-$C_{10}$ alkoxy" means the group R'O—, wherein R' is $C_1$-$C_{10}$ alkyl and has the meanings defined above. Examples of $C_1$-$C_{10}$ alkoxy groups are methoxy, ethoxy, n-propoxy, isopropoxy, n-butoxy, isobutoxy, sec.-butoxy and tert.-butoxy, preferably methoxy and ethoxy.

In another embodiment, in the multifunctionalized silicon nanoparticles as defined above, Li has as a backbone a straight- or branched-chain unsubstituted or substituted $C_1$-$C_{12}$ alkyl chain, $C_2$-$C_{12}$ alkenyl chain, or a 1 to 12 atom chain consisting of carbon atoms, substituted carbon atoms and/or one or more atoms selected from O, N and S, or a chain as described before with the backbone containing one or more cyclic or heterocyclic aromatic or non-aromatic ring systems.

In one embodiment $L_1$ is a linker comprising a $C_1$-$C_{10}$ alkyl chain or an arylalky chain with 8 to 20 carbon atoms.

In one embodiment, $L_1$ is a linker comprising a $C_1$-$C_{10}$ alkyl chain, $C_2$-$C_{10}$ alkenyl chain, $C_1$-$C_{10}$ alkoxy chain, —$C_1$-$C_{10}$ alkyl-CONH—, —$C_1$-$C_{10}$ alkyl-NHCO—, or a substituted or unsubstituted 5- or 6-membered aromatic ring.

In a particular preferred embodiment $L_1$ is —$CH_2$—$CH_2$— or —$CH_2$—$CH_2$—$CH_2$—.

In another embodiment, in the multifunctionalized silicon nanoparticles as defined above, $L_2$ is a linker that is formed by reaction of a heterobifunctional crosslinker, which is heterobifunctional, e.g. for binding to sulfhydryl groups and to amino groups, respectively.

Preferably, the heterobifunctional crosslinker is selected from the group consisting of NHS-maleimide crosslinkers, which are based on N-hydroxysuccinimide and maleimide reactive groups; succinimidyl-(PEG)n NHS-PEG-maleimide crosslinkers, NHS-haloacetyl crosslinkers; and NHS-pyridyldithiol crosslinkers. In a particular preferred embodiment the heterobifunctional crosslinker is a succinimidyl-(PEG)n NHS-PEG-maleimide crosslinker.

As defined herein the term "reactive group" means any group, which is suitable for reacting with amine groups, preferably an N-hydroxysuccinimide group or a maleimide group, in order to bind a linker to an amino group; or a group, which is suitable for a second functionality binding, e.g. for reacting with an SH-group, preferably a maleimide group in order to bind a linker to an SH-group.

In a particular preferred embodiment, $L_2$ is a linker, which is formed by reaction of a heterobifunctional crosslinker selected from the group consisting of NHS-maleimide crosslinkers, e.g.

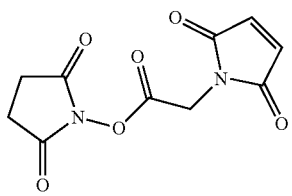

AMAS (N-α-maleimidoacet-oxysuccinimide ester)

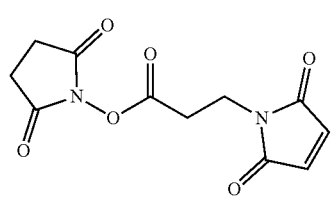

BMPS (N-β-maleimidopropyl-oxysuccinimide ester)

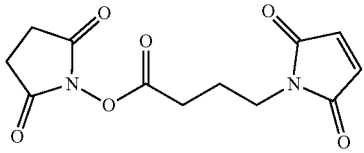

GMBS (N-γ-maleimidobutyryl-oxysuccinimide ester)

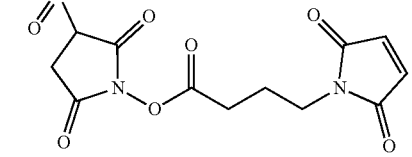

Sulfo-GMBS (N-γ-maleimidobutyryl-oxysulfosuccinimide ester)

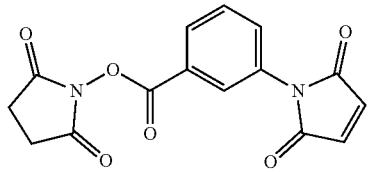

MBS (m-maleimidobenzoyl-N-hydroxysuccinimide ester)

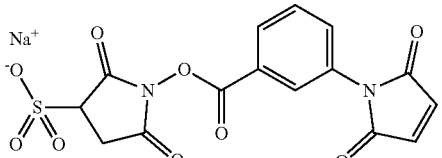

Sulfo-MBS (m-maleimidobenzoyl-N-hydroxysulfosuccinimide ester)

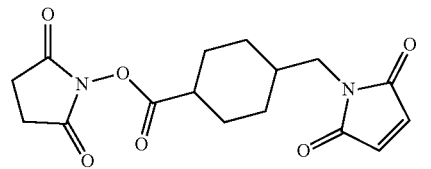

SMCC (succinimidyl 4-(N-maleimidomethyl)cyclohexane-1-carboxylate)

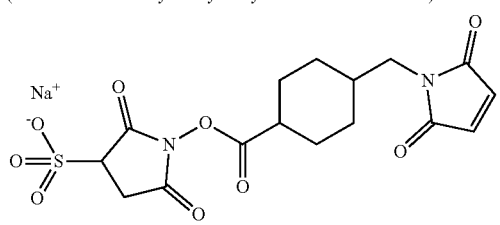

Sulfo-SMCC (sulfosuccinimidyl 4-(N-maleimidomethyl)cyclohexane-1-carboxylate)

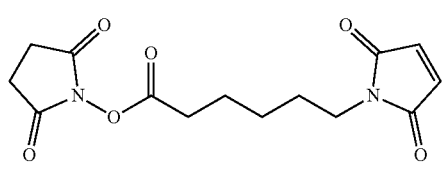

EMCS (N-ε-malemidocaproyl-oxysuccinimide ester)

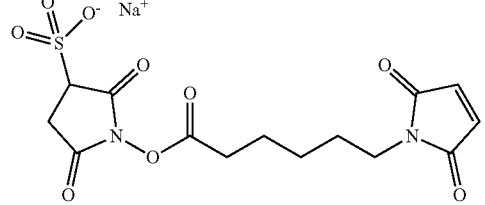

Sulfo-EMCS (N-ε-maleimidocaproyl-oxysulfosuccinimide ester)

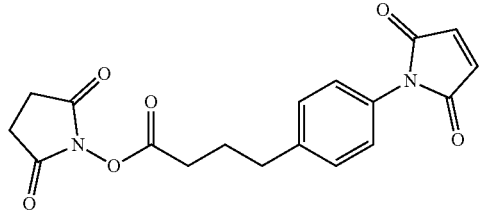

SMPB (succinimidyl 4-(p-maleimidophenyl)butyrate)

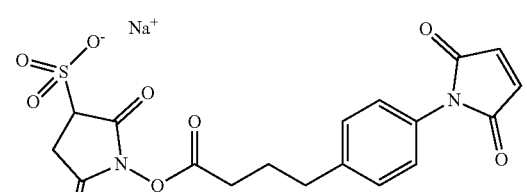

Sulfo-SMPB (sulfosuccinimidyl 4-(N-maleimidophenyl)butyrate)

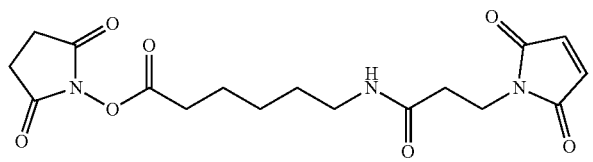

SMPH (Succinimidyl 6-((beta-maleimidopropionamido)hexanoate))

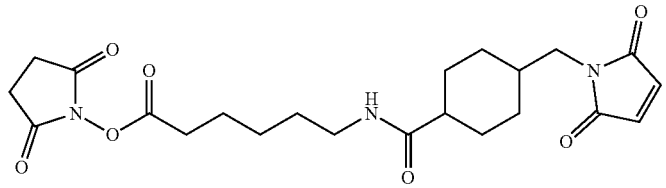

LC-SMCC (succinimidyl 4-(N-maleimidomethyl)cyclohexane-1-carboxy-(6-amidocaproate))

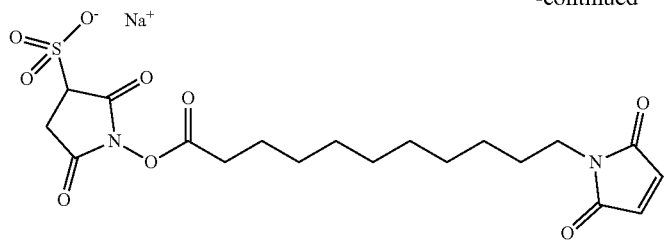

Sulfo-KMUS (N-κ-maleimidoundecanoyl-oxysulfosuccinimide ester)

succinimidyl-(PEG)n-maleimide or NHS-PEG-maleimide crossliners, e.g.

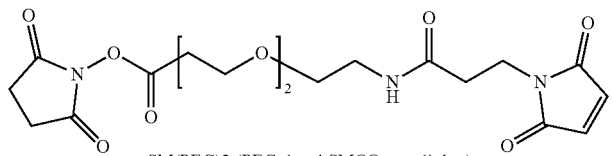

SM(PEG)2 (PEGylated SMCC crosslinker)
NHS-PEGn-Maleimide
Succinimidyl-([N-maleimidopropionamido]-di-ethyleneglycol) ester

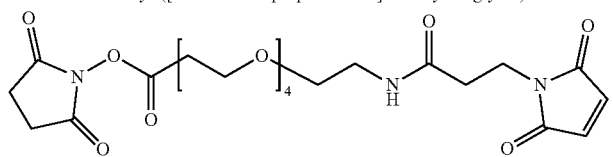

SM(PEG)4 (PEGylated SMCC crosslinker)
NHS-PEGn-Maleimide
Succinimidyl-([N-maleimidopropionamido]-tetra-ethyleneglycol) ester

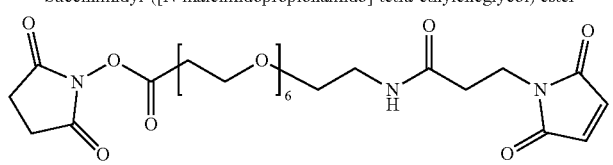

SM(PEG)6 (PEGylated, long-chain SMCC crosslinker)
NHS-PEGn-Maleimide
Succinimidyl-([N-maleimidopropionamido]-hexa-ethyleneglycol) ester

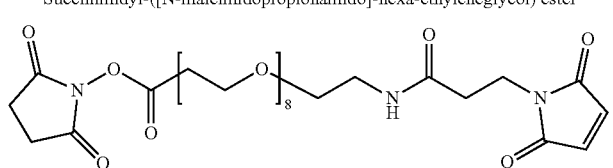

SM(PEG)8 (PEGylated, long-chain SMCC crosslinker)
NHS-PEGn-Maleimide
Succinimidyl-([N-maleimidopropionamido]-octa-ethyleneglycol) ester

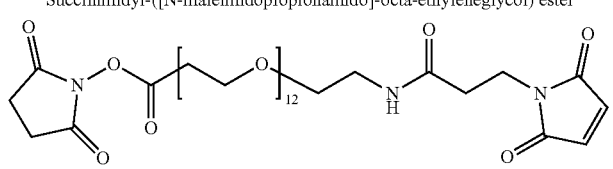

SM(PEG)12 (PEGylated, long-chain SMCC crosslinker)
NHS-PEGn-Maleimide
Succinimidyl-([N-maleimidopropionamido]-dodeca-ethyleneglycol) ester

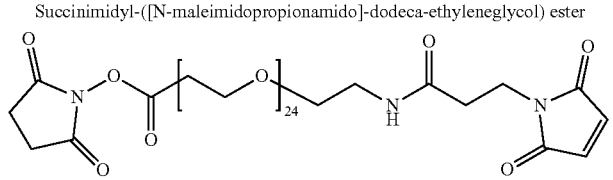

SM(PEG)24 (PEGylated, long-chain SMCC crosslinker)
NHS-PEGn-Maleimide
Succinimidyl-([N-maleimidopropionamido]-twentyfour-ethyleneglycol) ester -continued NHS-haloacetyl crosslinker, e.g.

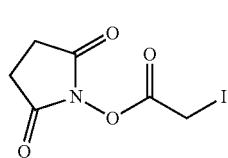
SIA (succinimidyl iodoacetate)

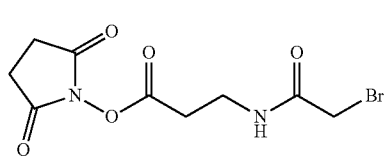
SBAP (succinimidyl 3-(bromoacetamido)propionate)

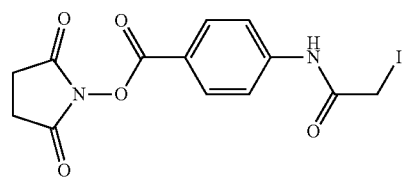
SIAB (succinimidyl (4-iodoacetyl)aminobenzoate)

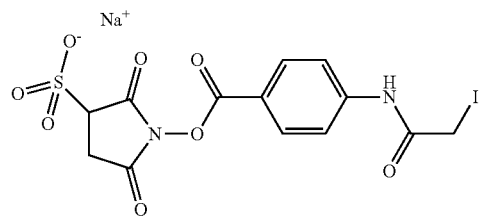
Sulfo-SIAB (sulfosuccinimidyl (4-iodoacetyl)aminobenzoate)

and NHS-pyridyldithiol crosslinkers, e.g.

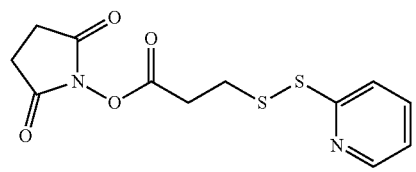
SPDP Succinimidyl 3-(2-pyridyldithiol)propionate

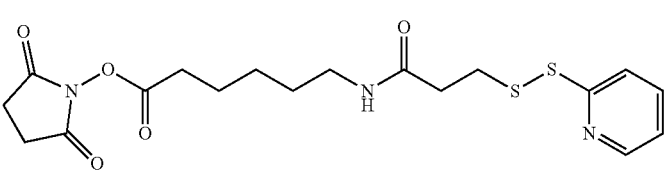
LC-SPDP Succinimidyl 6-[3(2-pyridyldithiol)propionamido]hexanoate

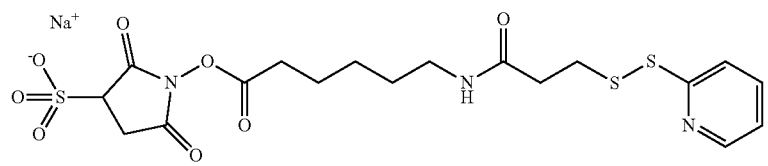
Sulfo-LC-SPDP (sulfosuccinimidyl 6-(3'-(2-pyridyldithio)propionamido)hexanoate)

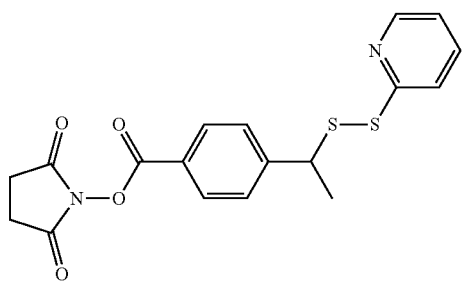
SMPT (4-succinimidylocycarbonyl-alpha-methyl-α(2-pyridyldithio)toluene)

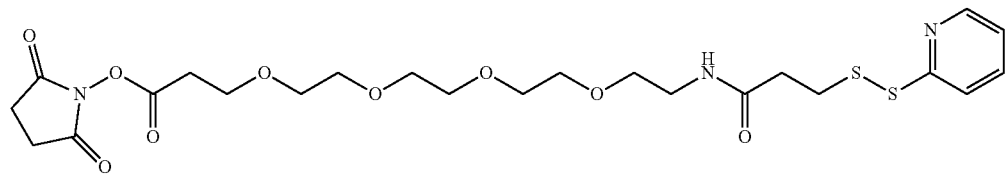
PEG4-SPDP (PEGylated, long-chain SPDP crosslinker)

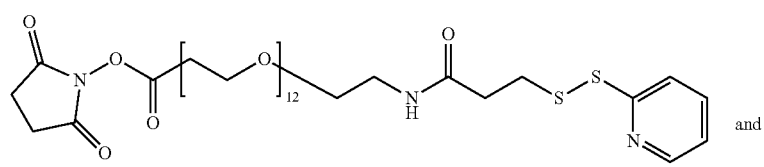 and

PEG12-SPDP (PEGylated, long-chain SPDP crosslinker)

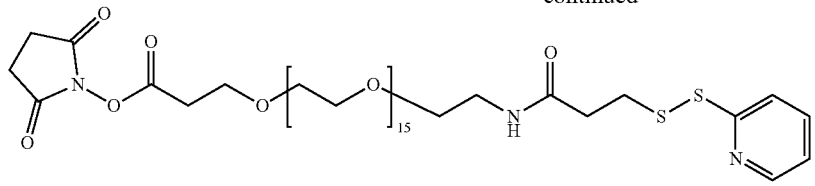

alpha-[3-(o-Pyridyldisulfido)propanoylamido]-omega-(succinimidyl propionate) hexadeca(ethylene glycol)

In one embodiment, in the multifunctionalized silicon nanoparticles as defined above, R is H, —CO-$L_2$ with one The surface modification reagents may be e.g. selected from the following reagents:

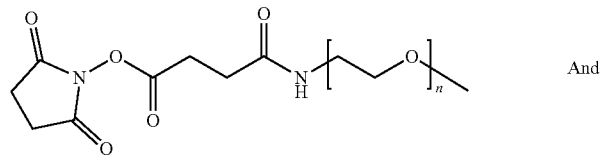

NHS-PEGn-OMe
O-[(N-Succinimidyl)succinyl-aminoethyl]-O-methylpolyethylene glycol
n = 6
n = 12
n = 18
n = 24
2000 Da
5000 Da
10000 Da And

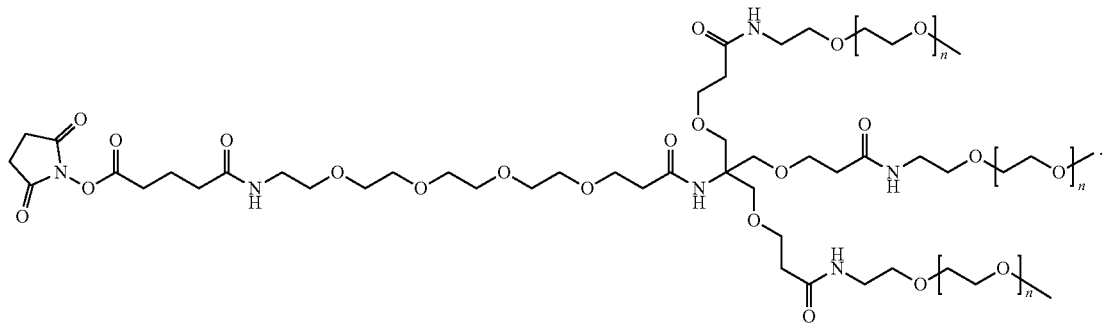

n = 12: NHS-PEG4-(PEG12)3
n = 7: NHS-PEG4-(PEG7)3 reactive group, —CO-deactivated $L_2$, wherein $L_2$ is as defined above, or a residue resulting from a NHS-PEGn-OMe surface modification reagent.

As defined herein, the term "—CO-$L_2$ with one reactive group" means a linker with one reactive group, resulting from reacting one reactive group of a heterobifunctional crosslinker, i.e. of an N-hydroxysuccinimide group via an amide group —CO—NH— to an amine-terminated $C_3$-$C_{18}$ aminoalkyl group, to an amine-terminated 3-(2-amino-ethoxy)-propyl group, to an amine-terminated 3-[2-(2-amino-ethoxy)-ethoxy]-propyl groups or to amine-terminated 2-(4-amino-methyl-phenyl)-ethyl group.

As defined herein, the term "—CO-deactivated $L_2$" means a linker resulting from quenching of the remaining activated group of the linker, e.g. a maleimide quenched with cysteine.

In one embodiment, M is an electrochemiluminescent (ECL) ruthenium, osmium, rhenium, europium, terbium, dysprosium or iridium complex.

In a preferred embodiment, M is an electrochemiluminescent (ECL) ruthenium or iridium complex.

ECL complexes in terms of the present invention are well known to the skilled person and include positively charged ECL complexes, negatively charged ECL complexes and electronically neutral ECL complexes.

Because of the cationic nature of the metal ion in a coordinating metal complex, the electronic neutrality of a label molecule is achieved by the counterion(s).

In one embodiment, M is an ECL complex with positively charged luminophores selected from the ECL complexes disclosed in WO 2003/002974 A2, U.S. Pat. Nos. 5,221,605 and 6,316,607, which are incorporated herein by reference in their entirety, the counterions are chloride, hexafluorophosphate etc.

In one embodiment, M is an ECL complex with negatively charged luminophores selected from the ECL complexes disclosed in U.S. Pat. No. 6,808,939, which is incorporated herein by reference in its entirety, the counterion is, e.g., sodium ion or proton.

In one embodiment, M is an electronically neutral ECL ruthenium complex selected from the ECL complexes disclosed in US 2016/0146826 A1, which is incorporated herein by reference.

In one embodiment, M is an ECL iridium complex selected from the ECL complexes disclosed in WO 2012/107419 A1, WO 2012/107420 A1, WO 2014/019707 A2, WO 2014/019708 A2, WO 2014/019709 A2, WO 2014/019710 A2 and WO 2014/019711 A2, which are incorporated herein by reference.

In a preferred embodiment, M is an ECL complex having a core structure selected from

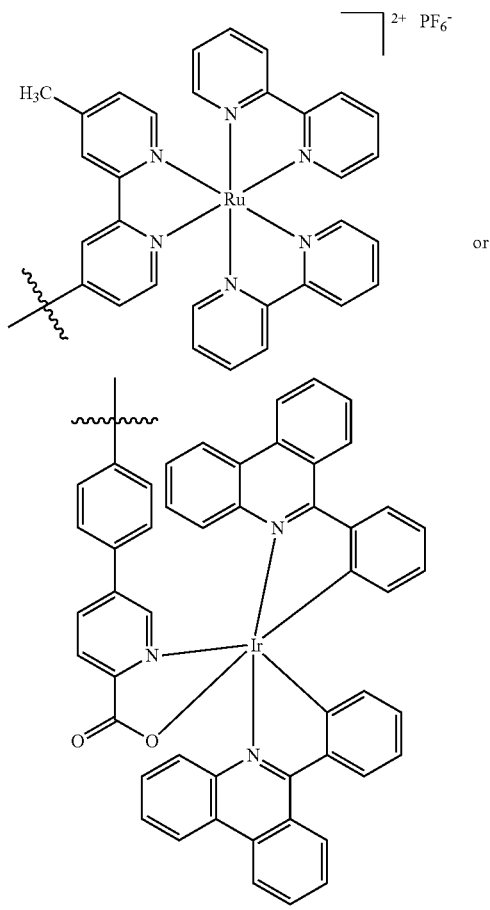

or

In a particular preferred embodiment, $L_1$-M is obtainable from one of the following metal complexes:

Ru(bpy)$_2$-bpyCO-OSu (CAS Reg. Nr. 137323-76-3,=Ruthenium(2+), bis(2,2'-bipyridine-kN$^1$,KN$^1$)[1-[4-(4'-methyl[2,2'-bipyridin]-4-yl-kN$^1$,kN$^1$)-1-oxobutoxy]-2,5-pyrrolidinedione]-, (OC-6-33) a reactive ester of Ru(bpy)$_2$-bpyCO$_2$H (=BPRu, or Ru-bpy), CAS Reg. Nr.115239-59-3)); or Sulfo-BPRu NHS Ester (=CAS Reg. Number 482618-42-8 also known in the art as ruthenate(2-), bis[[2,2'-bipyridine]-4,4'-dimethanesulfonato(2-)-kN$^1$,kN$^1$][1-[4-(4'-methyl[2,2'-bipyridin]-4-yl-kN$^1$,KN$^1$)-1-oxobutoxy]-2,5-pyrrolidinedione]-, sodium (1:2), (OC-6-31); or Ir(6-phenylphenanthridine)2-pyridine-2-carboxylic acid or a derivative thereof, including but not limited to, e.g. Ir(6-phenylphenanthridine)2-3-hydroxypyridine-2-carboxylic acid, Ir(6-phenylphenanthridine)2-4-(hydroxymethyl)pyridine-2-carboxylic acid, Ir(6-phenylphenanthridine)2-2-(carboxyethyl-phenyl)pyridine-2-carboxylic acid Ir(6-phenylphenanthridine)2-5-(methoxy)pyridine-2-carboxylic acid, or an Ir(6-phenylphenanthridine)2-2-(carboxyethyl-phenyl)pyridine-2-carboxylic acid ester, or derivatives of it like iridium complexes with ligands substituted with one or more sulfonic acids, or e.g. CAS registry number 1556730-07-4 (=1B3/47, also known in the art as Iridate(3-), [5-[4-(2-carboxyethyl)phenyl]-2-pyridinecarboxylato(2-)-kN$^1$, κO2]bis[2-(6-phenanthridinyl-κN)-5-(3-sulfonatopropoxy)phenyl-κC]-, cesium hydrogen (1:2:1) or the N-hydroxy succinimide ester thereof, or iridium complexes with two phenyl-phenanthridine ligands having two sulfonatopropoxy substituents, two sulfo-methyl, comprising 2,9-phenanthridinedimethanesulfonic acid, 6-phenyl-, sodium salt (CAS registry number 1554465-50-7) or two polyethylenglycol substituents, or three of each, or combinations thereof.

In one embodiment, the multifunctionalized silicon nanoparticles of the present invention correspond to Formula (I)

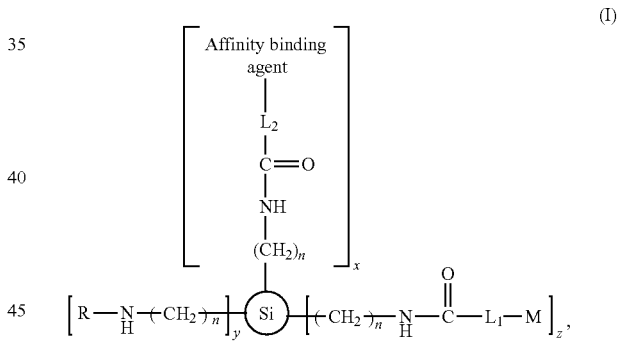

wherein n is 3, x is 1, y is at least 1, z is 1, $L_1$ is —CH$_2$—CH$_2$— or —CH$_2$—CH$_2$—CH$_2$—, $L_2$ is a linker as defined above, wherein $L_1$ and $L_2$ are identical or different, Si is a silicon core having a size of from 1 nm to 10 nm R is H, —CO-$L_2$ with one reactive group, —CO-deactivated $L_2$, wherein $L_2$ is as defined above, or a residue resulting from a surface modification reagent as defined above, and M is an electrochemiluminescent metal complex, or a salt thereof having a core structure selected from the group consisting of:

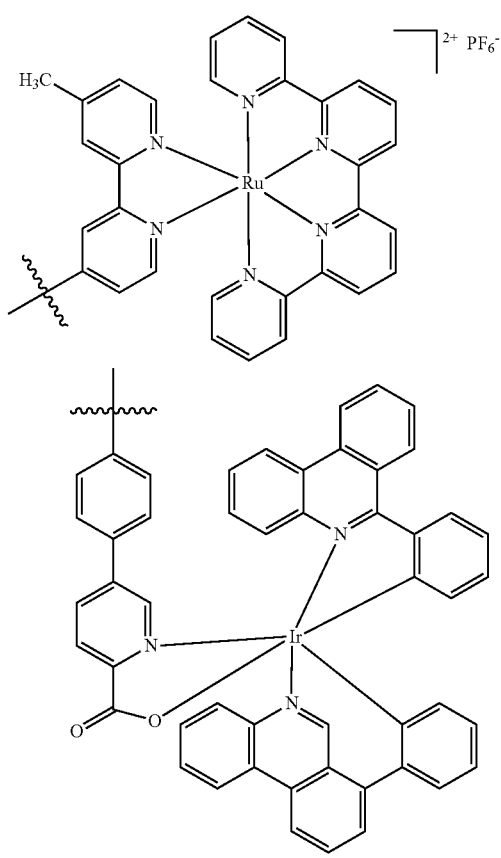

and

Any combinations of any of the embodiments as defined above are considered to be subject-matter of the present invention.

Processes for the Preparation of Multifunctionalized Silicon Nanoparticles of the Invention A problem of the invention was to provide processes for the preparation of multifunctionalized silicon nanoparticles, which allow tailoring the multifunctionalized silicon nanoparticles dependent on the desired use in immunoassays.

Therefore, the present invention, in one aspect, relates to novel processes for the preparation of multifunctionalized silicon nanoparticles.

Multifunctionalized silicon nanoparticles according to the invention can for example be prepared by the following two processes.

Process I: In cases where the affinity binding agent is a low molecular weight analyte or a derivative thereof, the process of the invention comprises at least the following steps:

(a) reacting amine-terminated $C_3$-$C_{18}$ aminoalkyl silicon nanoparticles, amine-terminated 3-(2-amino-ethoxy)-propyl silicon nanoparticles, amine-terminated 3-[2-(2-amino-ethoxy)-ethoxy]-propyl silicon nanoparticles or amine-terminated 2-(4-amino-methyl-phenyl)-ethyl silicon nanoparticles with electrochemiluminescent compounds comprising an activated linker, if appropriate in the presence of a solvent, and if appropriate in the presence of a coupling reagent,
to obtain amine-terminated $C_3$-$C_{18}$ aminoalkyl silicon nanoparticles, amine-terminated 3-(2-amino-ethoxy)-propyl silicon nanoparticles, amine-terminated 3-[2-(2-amino-ethoxy)-ethoxy]-propyl silicon nanoparticles or amine-terminated 2-(4-amino-methyl-phenyl)-ethyl silicon nanoparticles, which are in each case covalently bound to 1 to 100 electrochemiluminescent compounds via a linker, and (b) reacting the functionalized silicon nanoparticles obtained according to process step (a) with at least one affinity binding agent, which is covalently bound to an activated linker, if appropriate in the presence of a solvent, and if appropriate in the presence of a coupling reagent, thereby obtaining multifunctionalized silicon nanoparticles of the invention as described herein, wherein the affinity binding agent is a low molecular analyte or a derivative thereof as defined herein.

In one embodiment, in process I, the analyte comprised in the multifunctionalized silicon nanoparticles as defined above as an affinity binding agent is a low molecular weight analyte, i.e. it has a molecular weight of 2000 Dalton or less. Preferred analytes comprised in such multifunctionalized silicon nanoparticles are physiologically/diagnostically relevant hormones or metabolites.

Physiologically/diagnostically relevant hormones or metabolites include folate, especially the so-called total folate as comprised in both the blood plasma and in the red blood cells, steroids like estradiol, estrone, progesterone, 17-hydroxyprogesterone, cortisol, testosterone, androstendione, hormones like 25-hydroxy vitamin D3.

Process II: In cases where the affinity binding agent comprises an amino group, e.g. if the affinity binding agent is a protein, the process of the invention comprises at least the following steps:

(a) reacting amine-terminated $C_3$-$C_{18}$ aminoalkyl silicon nanoparticles, amine-terminated 3-(2-amino-ethoxy)-propyl silicon nanoparticles, amine-terminated 3-[2-(2-amino-ethoxy)-ethoxy]-propyl silicon nanoparticles or amine-terminated 2-(4-amino-methyl-phenyl)-ethyl silicon nanoparticles with electrochemiluminescent compounds comprising an activated linker, if appropriate in the presence of a solvent, and if appropriate in the presence of a coupling reagent,
to obtain amine-terminated $C_3$-$C_{18}$ aminoalkyl silicon nanoparticles, amine-terminated 3-(2-amino-ethoxy)-propyl silicon nanoparticles, amine-terminated 3-[2-(2-amino-ethoxy)-ethoxy]-propyl silicon nanoparticles or amine-terminated 2-(4-amino-methyl-phenyl)-ethyl silicon nanoparticles, which are in each case covalently bound to 1 to 100 electrochemiluminescent compounds via a linker but still comprise terminal amino groups, (b) reacting the functionalized silicon nanoparticles obtained according to process step (a) with a heterobifunctional crosslinker comprising a first reactive group for binding to amino groups and a second reactive group for binding e.g. to an SH— group, thereby binding the linker via the first (amine-) reactive group to one or more of the terminal amino groups to obtain functionalized silicon nanoparticles comprising 1 to 100 electrochemiluminescent compounds as well as one or more activated linker(s) still comprising the second reactive group (e.g. the SH-reactive functionality), and (c) reacting the functionalized silicon nanoparticles obtained according to process step (b) with a protein, thereby binding the protein via the second reactive group to the affinity binding agent, to obtain one embodiment of multifunctionalized silicon nanoparticles of the present invention as defined herein.

The amine-terminated $C_3$-$C_{18}$ aminoalkyl silicon nanoparticles, amine-terminated 3-(2-amino-ethoxy)-propyl silicon nanoparticles, amine-terminated 3-[2-(2-aminoethoxy)-ethoxy]-propyl silicon nanoparticles and amine-terminated 2-(4-amino-methyl-phenyl)-ethyl silicon nanoparticles used as a starting material in process step (a) of processes I and II may be prepared by processes as described e.g. by M. Rosso-Vasic, Journal of Materials Chemistry (2009), 19(33), 5926-5933. Alternatively, they may be obtained as described in WO 2013/087734 A2 or by Y. Zhong, Journal of American Chemical Society (2013), 135, 8350-8356.

Suitable monomers for the preparation of the amine-terminated silicon nanoparticles include but are not limited to 2-propen-1-amine, 3-buten-1-amine, 4-penten-1-amine, 5-hexen-1-amine, 6-hepten-1-amine, 7-octen-1-amine, 8-nonen-1-amine, 9-decen-1-amine, 10-undecen-1-amine, 11-dodecen-1-amine, 17-octadecen-1-amine, 2-(2-propen-1-yloxy)-ethanamine, 2-[-(2-propen-1-yloxy)ethoxy]-ethanamine and 4-ethenylbenzenmethanamine.

The electrochemiluminescent compounds comprising an activated linker used as a starting material in process step (a) of processes I and II are well known to the skilled person and are commercially available or can be prepared according to process described in the state of the art. Electrochemiluminescent compounds comprising an activated linker are e.g. disclosed in US 2016/0146826 A1, WO 2014/019707 A2, WO 2014/019708 A2, WO 2014/019709 A2, WO 2014/019710 A2 and WO 2014/019711 A2, which are incorporated herein by reference in their entirety.

In one embodiment, the electrochemiluminescent compounds comprising an activated linker are selected from the group consisting of Ru(bpy)$_2$-bpyCO-OSu a reactive ester of Ru(bpy)$_2$-bpyCO$_2$H (=BPRu), which is the N-hydroxy-succinimide ester of CAS Reg. Nr.115239-59-3 also known in the art as ruthenium(1+), bis(2,2'-bipyridine-KN1,KN1')(4'-methyl[2,2'-bipyridine]-4-butanoato-KN1,KN1')-, (OC-6-33)-, hydrogen hexafluorophosphate(1-) (1:1:2), also known as ruthenium (1+), bis(2,2'-bipyridine-N,N')(4'-methyl[2,2'-bipyridine]-4-butanoato-N1,N1')-, (OC-6-33)-, hydrogen hexafluorophosphate(1-) (1:1:2)); or Sulfo-BPRu NHS Ester (=CAS Reg. Number 482618-42-8 also known in the art as ruthenate(2-), bis[[2,2'-bipyridine]-4,4'-dimethanesulfonato(2-)-kN1,kN1'][1-[4-(4'-methyl[2,2'-bipyridin]-4-yl-κN1,κN1')-1-oxobutoxy]-2,5-pyrrolidinedione]-, sodium (1:2), (OC-6-31), further known as ruthenate(2-), bis[[2,2'-bipyridine]-4,4'-dimethanesulfonato(2-)-κN1,κN1'][1-[4-(4'-methyl[2,2'-bipyridin]-4-yl-κN1,κN1')-1-oxobutoxy]-2,5-pyrrolidinedione]-, disodium, (OC-6-31)-(9Cl)); and A reactive NHS ester of Ir(6-phenylphenanthridine)2-pyridine-2-carboxylic acid or a derivative thereof, including but not limited to, e.g. Ir(6-phenylphenanthridine)2-3-hydroxypyridine-2-carboxylic acid, Ir(6-phenylphenanthridine)2-4-(hydroxymethyl)pyridine-2-carboxylic acid, Ir(6-phenylphenanthridine)2-2-(carboxyethyl-phenyl)pyridine-2-carboxylic acid Ir(6-phenylphenanthridine)2-5-(methoxy) pyridine-2-carboxylic acid, or an Ir(6-phenylphenanthridine)2-2-(carboxyethyl-phenyl)pyridine-2-carboxylic acid ester, or derivatives of it like iridium complexes with ligands substituted with one or more sulfonic acids, or e.g. CAS registry number 1556730-07-4 (=IB3/47, also known in the art as Iridate(3-), [5-[4-(2-carboxyethyl)phenyl]-2-pyridinecarboxylato(2-)-κN1,κO2]bis[2-(6-phenanthridinyl-κN)-5-(3-sulfonatopropoxy) phenyl-κC]-, cesium hydrogen (1:2:1) or the N-hydroxy succinimide ester thereof, or iridium complexes with two phenyl-phenanthridine ligands having two sulfonatopropoxy substituents, two sulfo-methyl, comprising 2,9-phenanthridinedimethanesulfonic acid, 6-phenyl-, sodium salt (CAS registry number 1554465-50-7) or two polyethylenglycol substituents, or three of each, or combinations thereof.

Process step (a) of processes I and II is carried out under standard coupling conditions. Appropriate solvents and appropriate coupling reagents are well known to the skilled person.

Affinity binding agents, which are covalently bound to an activated linker used as starting material in process step (b) of process I are well known to the skilled person. Alternatively, they can be prepared by reacting an affinity binding agent with a commercially available heterobifunctional crosslinker, e.g. with any of the heterobifunctional crosslinkers described above. Examples of affinity binding agents, which are covalently bound to an activated linker include but are not limited to the following analyte-activated linkers:

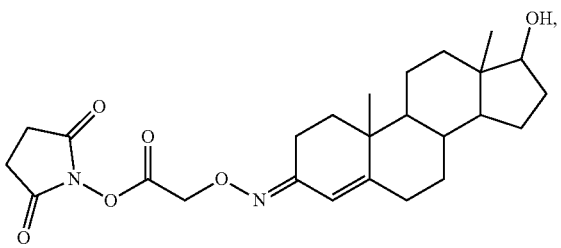

testosterone-3-carboxymethoxim-N-hydroxysuccinimide ester

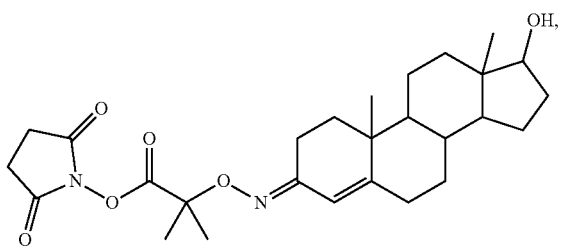

testosterone-3-dimethyl-carboxymethoxim-N-hydroxysuccinimide ester

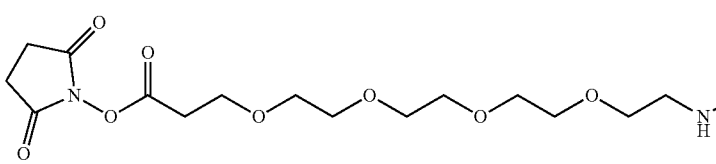

-continued
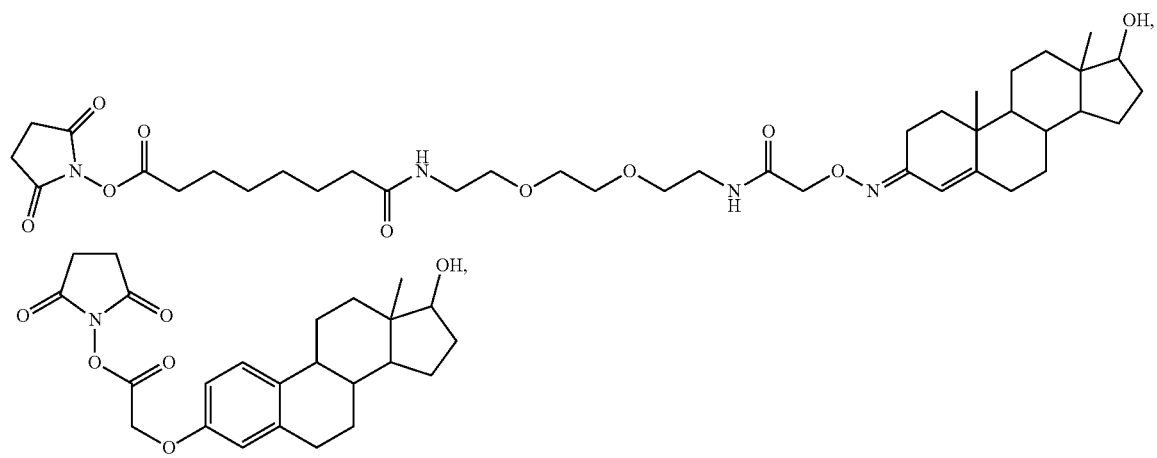
estradiol-3-carboxymethylether-N-hydroxysuccinimide ester
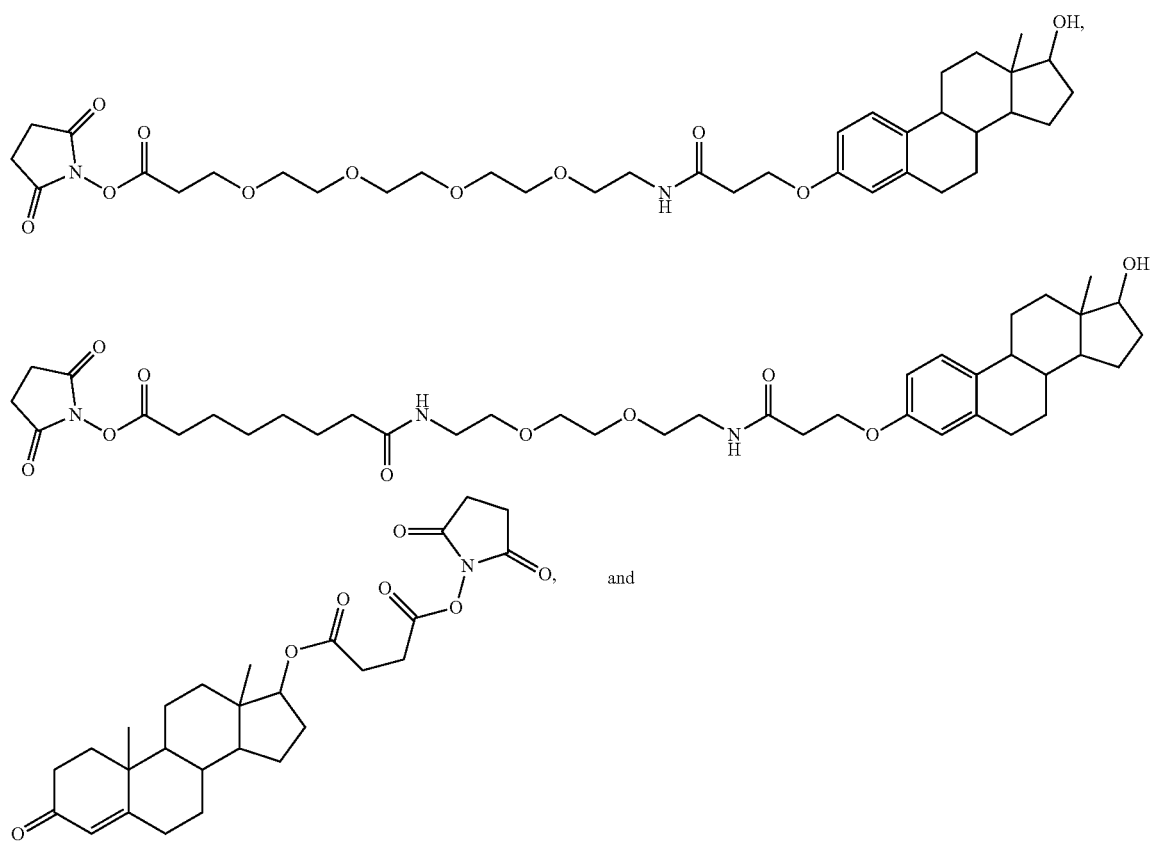
testosterone-17-hemisuccinat-N-Hydroxysuccinimide ester
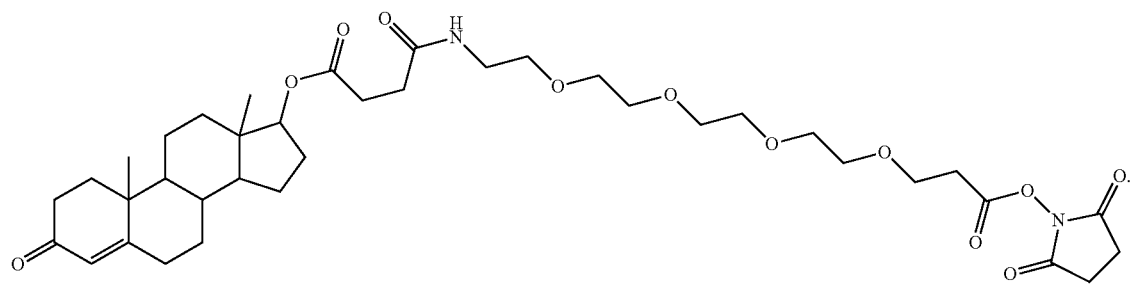

Process step (b) of processes I and II and process step (c) of process (c) are carried out under standard coupling conditions. Appropriate solvents and appropriate coupling reagents are well known to the skilled person. Appropriate solvents and appropriate coupling reagents, are well known to the skilled person.

In embodiment, process I for the preparation of multifunctionalized silicon nanoparticles of Formula (I)

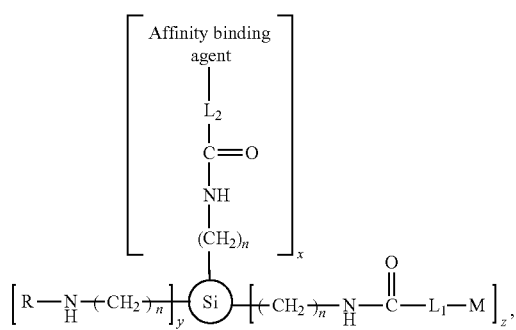

wherein n, x, y, z, $L_1$, $L_2$, Si, M and the affinity binding agent are defined as above and R is H, comprising at least the following steps:

(a) reacting amine-terminated silicon nanoparticles of the Formula (II)

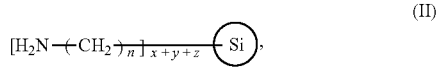

wherein n, x, y, z and Si are defined as above, with z activated linker-ECL-metal complexes of the Formula (III)

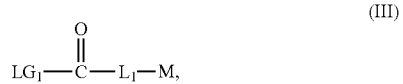

wherein $L_1$ and M are defined as above, and $LG_1$-CO— is a reactive group for binding to amino groups, preferably $LG_1$-CO is a succinimidyl-O—CO group, if appropriate in the presence of a solvent, and if appropriate in the presence of a coupling agent to obtain functionalized silicon nanoparticles of the Formula (IV)

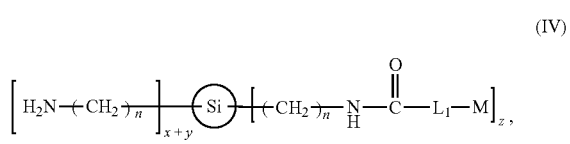

wherein n, y, Si, Li and M are as defined as above, and (b) reacting the functionalized silicon nanoparticles of the Formula (IV) with x activated linker-affinity binding agents of the Formula (V)

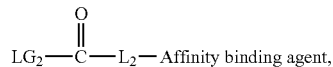

wherein $L_2$ and the affinity binding agent are as defined above and $LG_2$ is a reactive group for binding to amino groups, preferably $LG_2$-CO is a succinimidyl-O—CO group, to obtain multifunctionalized silicon nanoparticles of the Formula (I) as defined above, wherein R is H.

In process I, $LG_1$ and $LG_2$ may be identical or different.

The amine-terminated silicon nanoparticles of the Formula (II) used as starting material in process step (a) may be prepared by processes as described e.g. by M. Rosso-Vasic, Journal of Materials Chemistry (2009), 19(33), 5926-5933. Alternatively, they may be obtained as described in WO 2013/087734 A2 and by Y. Zhong, Journal of American Chemical Society (2013), 135, 8350-8356.

Suitable monomers for the preparation of the amine-terminated silicon nanoparticles of the Formula (II) include but are not limited to 2-propen-1-amine, 3-buten-1-amine, 4-penten-1-amine, 5-hexen-1-amine, 6-hepten-1-amine, 7-octen-1-amine, 8-nonen-1-amine, 9-decen-1-amine, 10-undecen-1-amine, 11-dodecen-1-amine, 17-octadecen-1-amine, 2-(2-propen-1-yloxy)-ethanamine, 2-[-(2-propen-1-yloxy)ethoxy]-ethanamine and 4-ethenylbenzenmethanamine.

The activated linker-ECL-metal complexes of the Formula (III) used as starting material in process step (a) are well known to the skilled person. Activated linker-ECL-metal complexes of the Formula (III) are e.g. disclosed in US 2016/0146826 A1, WO 2014/019707 A2, WO 2014/019708 A2, WO 2014/019709 A2, WO 2014/019710 A2 and WO 2014/019711 A2, which are incorporated herein by reference in their entirety.

Process step (a) is carried out under standard coupling conditions. Appropriate solvents and appropriate coupling reagents are well known to the skilled person. In a preferred embodiment N,N-dimethylformamide (DMF) is used as a solvent. Examples 2 and 3 show how functionalized silicon nanoparticles of the Formula (IV) can be obtained by process step (a).

The functionalized silicon nanoparticles of the Formula (IV) are novel. Therefore, in one aspect, the present invention relates to functionalized silicon nanoparticles of the Formula (IV) as defined above.

Activated linker-affinity binding agents of the Formula (V) used as starting material in process step (b) are well known to the skilled person. Alternatively, they can be prepared by reacting an affinity binding agent as defined above with a commercially available heterobifunctional crosslinker, e.g. with any of the heterobifunctional crosslinkers described above. Examples of activated linker-affinity binding agents of the Formula (V) include but are not limited to the analyte-activated linkers described above.

Process step (b) is also carried out under standard coupling conditions. Appropriate solvents and appropriate coupling reagents, are well known to the skilled person.

In one embodiment, process I further comprises the step of (c) reacting multifunctionalized silicon nanoparticles of the Formula (I) as defined above, wherein R is H with a compound of the Formula (VI)

(VI)

wherein CO-LG$_3$ is a reactive group for binding to amino groups, preferably LG$_3$-CO is a succinimidyl-O—CO group, and R"—CO— is L$_2$ as defined above, deactivated L$_2$ as defined above or a surface modification reagent as defined above, preferably generated by a reaction with an NHS-PEGn-OMe surface modification reagent, to obtain multifunctionalized silicon nanoparticles of the Formula (I), wherein R is L$_2$ as defined above, deactivated L$_2$ as defined above or a residue of a surface modification reagent as defined above.

Compounds of the Formula (VI) used as starting material in process step (c) are well known to the skilled person.

As indicated above—in cases where the affinity binding agent comprises an amino group an approach as described under process II has to be taken.

Thus, in one embodiment, process II for the preparation of multifunctionalized silicon nanoparticles of Formula (I)

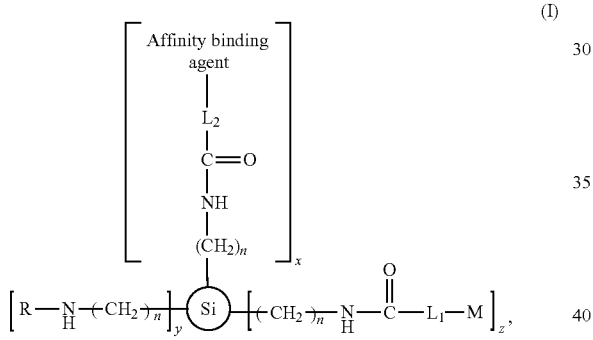
(I)

wherein n, x, y, z, L$_1$, L$_2$, Si, M are defined as above, the affinity binding agent is as defined above and comprises an amino group, and R is H, —CO-L$_2$ with one reactive group, —CO-deactivated L$_2$ comprises at least the following steps:

(a) reacting amine-terminated silicon nanoparticles of the Formula (II)

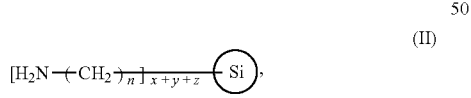
(II)

wherein n, x, y, z and Si are defined as above,
with z activated linker-ECL-metal complexes of the Formula (III)

(III)

wherein L$_1$ and M are defined as above, and LG$_1$-CO— is a reactive group for binding to amino groups, preferably LG$_1$-CO is a succinimidyl-O—CO group, if appropriate in the presence of a solvent, and if appropriate in the presence of a coupling agent to obtain functionalized silicon nanoparticles of the Formula (IV)

(IV)

wherein n, x, y, z, Si, L$_1$ and M are as defined as above, (b) reacting the functionalized silicon nanoparticles of the Formula (IV) with x heterobifunctionalized cross-linkers of the Formula (VII)

(VII)

wherein LG$_4$ is a reactive group for binding to amino groups, preferably LG$_4$-CO is a succinimidyl-O—CO group, and RG is a reactive group suitable for binding e.g. to an SH group, if appropriate in the presence of a solvent, and if appropriate in the presence of a coupling agent to obtain functionalized silicon nanoparticles of the Formula (VIII)

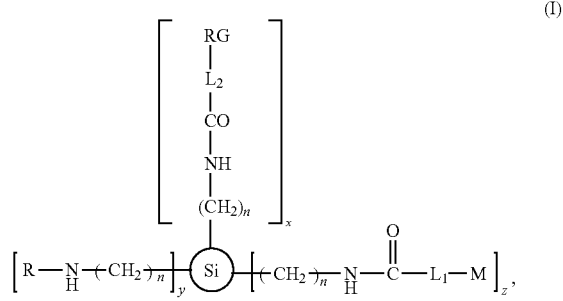
(I)

wherein n, x, y, z, L$_1$, L$_2$, Si, M and RG are as defined above, (c) reacting the functionalized silicon nanoparticles of the Formula (VIII) obtained according to process step (b) if appropriate in the presence of a solvent with an affinity binding agent comprising e.g. a thiol group, e.g. with a protein to obtain multifunctionalized silicon nanoparticles of Formula (I), wherein n, x, y, z, L$_1$, L$_2$, Si, and M are defined as above, the affinity binding agent is as defined above and comprises an amino group, and R is H, —CO-L$_2$ with one reactive group, —CO-deactivated L$_2$.

The amine-terminated silicon nanoparticles of the Formula (II) used as starting material in process step (a) may be prepared by processes as described above.

The activated linker-ECL-metal complexes of the Formula (III) used as starting material in process step (a) are as indicated above.

In one embodiment, process II further comprises the step of
(d) reacting multifunctionalized silicon nanoparticles of the Formula (I) as defined above, wherein R is H with a compound of the Formula (VI)

wherein CO-LG$_3$ is a reactive group for binding to amino groups, preferably LG$_3$-CO is a succinimidyl-O—CO group, and R″—CO— is L$_2$ as defined above, deactivated L$_2$ as defined above or a surface modification reagent as defined above, preferably generated by a reaction with an NHS-PEGn-OMe surface modification reagent, to obtain multifunctionalized silicon nanoparticles of the Formula (I), wherein R is L$_2$ as defined above, deactivated L$_2$ as defined above or a residue of a surface modification reagent as defined above.

Process steps (a), (b), (c) and (d) are also carried out under standard coupling conditions. Appropriate solvents and appropriate coupling reagents, are well known to the skilled person.

Uses of the Multifunctionalized Silicon Nanoparticles of the Invention

The inventors have now surprisingly and unexpectedly found that the multifunctionalized silicon nanoparticles as defined above have quite favorable properties. For example, the multifunctionalized silicon nanoparticles show a high ECL efficiency. This high efficiency is also present if the corresponding measurements are performed in an aqueous system as compared to many ECL-labels that only have shown high ECL-efficiency when analyzed in an organic solvent. E.g., many electrochemiluminescent molecules usually are analyzed in acetonitrile and either are not soluble in an aequeous solution or, if soluble, do not show efficient electrochemiluminescence in an aequeous solution.

Furthermore, it has been found that the multifunctionalized silicon nanoparticles can be adapted to meet the needs of an ECL-based immunoassays since the physical and chemical properties of the multifunctionalized silicon nanoparticles can be tailored dependent on the requirements of the test format.

Therefore, in one aspect, the present invention relates to the use of multifunctionalized silicon nanoparticles as defined above in electrochemiluminescence based detection methods.

In another aspect, the present invention relates to the use of multifunctionalized silicon nanoparticles as defined above for performing an electrochemiluminescence reaction in an aqueous solution.

An aqueous solution is any solution comprising at least 90 wt. % water (weight by weight). Obviously such aqueous solution may contain in addition ingredients like buffer compounds, detergents and for example tertiary amines like tripropylamine as electron donor in the ECL reaction, as for example in the commercially available ProCell solution.

In another aspect, the present invention relates to the use of multifunctionalized silicon nanoparticles as defined above in the in vitro detection of an analyte as defined herein.

In another aspect, the present invention relates to a composition comprising multifunctionalized silicon nanoparticles as defined above. The composition may be used for the detection of an analyte of interest present in a sample.

Methods for Measuring an Analyte employing Multifunctionalized Silicon Nanoparticles of the Invention In another aspect, the present invention relates to a method for measuring an analyte by an in vitro method, the method comprising the steps of:
(a) providing a sample suspected or known to comprise the analyte,
(b) contacting said sample with multifunctionalized silicon nanoparticles as defined above, under conditions appropriate for the formation of a complex of the analyte with the multifunctionalized silicon nanoparticles to obtain an analyte-multifunctionalized silicon nanoparticle complex, and
(c) measuring the analyte-multifunctionalized silicon nanoparticle complex formed in step (b) and thereby obtaining a measure of the analyte.

In another aspect, the present invention relates to a method for measuring an analyte by an in vitro method, the method comprising the steps of:
(a) providing a sample suspected or known to comprise the analyte,
(b) contacting said sample with multifunctionalized silicon nanoparticles as defined above, wherein said nanoparticles comprise the analyte, with an analyte-specific affinity binding agent under conditions appropriate for the formation of a complex of multifunctionalized silicon nanoparticles and analyte-specific affinity binding agent to obtain an analyte-specific affinity binding agent-multifunctionalized silicon nanoparticle complex, and
(c) measuring the analyte-specific affinity binding agent-multifunctionalized silicon nanoparticle complex formed in step (b) and thereby obtaining a measure of the analyte.

In one embodiment, measuring an analyte means detecting the amount of an analyte in a sample.

In one embodiment, the measurement in the above methods for detection of an analyte is performed by using an electrochemiluminescence based detection procedure.

In a preferred embodiment, the methods of the invention are practiced in an aqueous solution.

The methods for measuring an analyte employing a multifunctionalized nanoparticle of the invention as defined above can be practiced according to state of the art procedures. Such methods may be constructed in a wide variety of formats known in the art such as sandwich assays and competitive binding assays (see, e.g., the following references: Nonradioactive Labeling and Detection of Molecules, Kessler, C., ed., Springer-Verlag: Berlin 1992; The Immunoassay Handbook, Wild, D., ed., Stackton Press: New York 1994; Keller, G. H. and Manak, M. M. DNA Probes, 2nd Ed., MacMillan Publishers Ltd.: London, 1993; Tietz Textbook of Clinical Chemistry 2nd Edition, Burtis et al. Ed., W. B. Saunders and Co.: Philadelphia, 1994).

As the person skilled in the art will readily appreciate the measuring of the analyte is usually made by generation of a signal, measurement of the signal generated and by calculating the concentration of the analyte from a standard curve for the analyte, i.e. thereby measuring the analyte. The assay component to which a label is usually attached, i.e. the multifunctionalized nanoparticles as defined above, comprises either an analyte-specific binding agent (sandwich-type assays) or the analyte (competitive type assays). Before the electrochemoluminescent label comprised in the multifunctionalized nanoparticles is measured, usually the multifunctionalized nanoparticles as defined above which are bound to a solid phase in such method are separated from the multifunctionalized nanoparticles not bound to the solid phase.

In one embodiment the methods of the present invention are practiced in a sandwich assay format.

In a typical sandwich-type assay, the analyte-specific binding agent bound to the second partner of the binding pair, and the detectably-labeled analyte-specific binding agent, respectively, each bind to the analyte at different and non-overlapping epitopes. A first analyte-specific binding agent (e.g. an antibody) is either covalently or passively bound to a solid surface. The solid surface is typically glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow for binding between the first or capture antibody and the corresponding antigen. Following the incubation period, the solid phase, comprising the first or capture antibody and bound thereto the antigen can be washed, and incubated with a secondary or labeled antibody binding to another epitope on the antigen. The second antibody is linked to a reporter molecule which is used to indicate the binding of the second antibody to the complex of first antibody and the antigen of interest. The later represents one specific embodiment of the multifunctionalized silicon nanoparticle as disclosed herein.

An extremely versatile alternative sandwich assay format includes the use of a solid phase coated with the first partner of a binding pair, e.g. paramagnetic streptavidin-coated microparticles. Such microparticles are mixed and incubated with an analyte-specific binding agent bound to the second partner of the binding pair, a sample suspected of comprising or comprising the analyte, wherein said second partner of the binding pair is bound to said analyte-specific binding agent, and a second analyte-specific binding agent which is detectably labeled, e.g. the multifunctionalized silicon nanoparticle as disclosed herein. As obvious to the skilled person these components are incubated under appropriate conditions and for a period of time sufficient for binding the multifunctionalized particles via the analyte, the analyte-specific binding agent (bound to) the second partner of the binding pair and the first partner of the binding pair to the solid phase microparticles. As appropriate such assay may include one or more washing step(s).

In a typical sandwich-type assay the analyte-specific binding agent bound to the second partner of the binding pair, and the detectably-labeled analyte-specific binding agent, respectively, each bind to the analyte at different and non-overlapping epitopes.

In one embodiment the methods of the present invention are practiced in a competitive assay format.

A typically competitive assay format makes use of a detectably labeled analyte. A multifunctionalized silicon nanoparticle comprising as an affinity binding agent the analyte represents one embodiment according to the present disclosure. In a competitive assay format the analyte comprised in the sample to be analyzed and a detectably labeled analyte compete for binding to an affinity binding agent, e.g. to a binding protein, a receptor, or an antibody. As the skilled person appreciates the analyte as such may be used and bound to the silicon nanoparticles, it is however also possible to use an analogue of the analyte in such procedure, e.g. a related substance or a fragment of the analyte as long as the affinity binding agent binds to both, the bound analyte-analogue and the free analyte in the sample to be investigated. Usually the affinity binding agent is directly or indirectly bound to a solid phase. After bound free-separation usually the bound fraction is analyzed and the signal generated is indirectly proportional to the concentration of the analyte in the sample, i.e. the higher the analyte concentration in the sample, the lower the signal measured.

The following examples are provided to aid the understanding of the present invention, the true scope of which is set forth in the appended claims. It is understood that modifications can be made in the procedures set forth without departing from the spirit of the invention.

All patents and publications identified herein are incorporated herein by reference in their entirety.

EXAMPLES

X-ray photoelectron spectroscopy (XPS), Transmission Electron Microscopy (TEM), Dynamic Light Scattering (DLS), Zeta potential measurements, UV-Vis absorption measurements, photoluminescence measurements, ECL and chronoamperometric measurements were carried out with standard measuring devices.

Example 1

Synthesis of Starting Materials 1.1 Synthesis of Amine-Terminated Silicon Nanoparticles Alkyl-functionalized silicon nanoparticles were prepared as described by M. Rosso-Vasic et al., Small (2008), 4(10), 1835-1841. Amine-terminated 3-aminopropyl silicon nanoparticles were prepared as described by J. H. Warner et al., Angewandte Chemie (2005), 117, 4626-4630; by M. Rosso-Vasic, Journal of Materials Chemistry (2009), 19(33), 5926-

5933; and by Y. Zhong, Journal of American Chemical Society (2013), 135, 8350-8356.

Example 2

Preparation and Characterization of [Ru]-labeled Silicon Nanoparticles and ECL Performance thereof 2.1 Preparation of [Ru]-labeled Silicon Nanoparticles

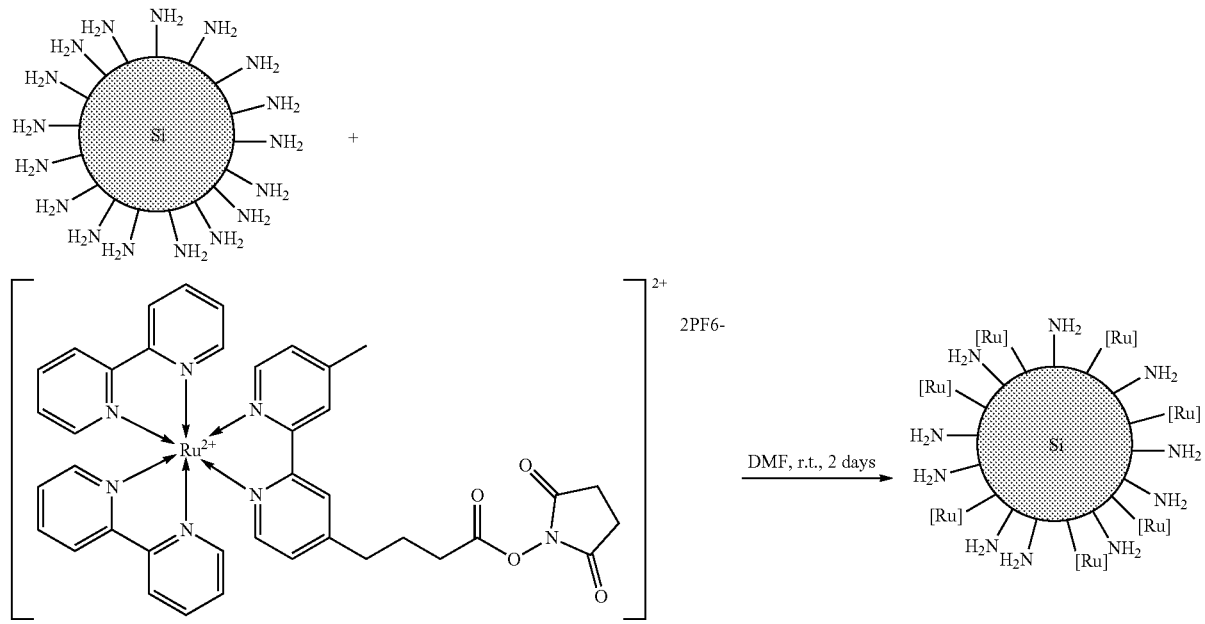

Rubpy-OSu (CAS Reg. Nr.115239-59-3, 57.6 mg, 54.5 µmol) were dissolved in 5 mL dried DMF in a 25 ml flask. Amine-terminated 3-aminopropyl silicon nanoparticles (1.8 mL in H$_2$O, 40 mg) were added slowly to the solution. Thereafter, the reaction mixture was stirred for 2 days under argon atmosphere at room temperature. Then, the solution was concentrated to about 2 ml solvent. The crude product was purified by dialysis (MWCO: 1000) for 6 hours against water. The water was exchanged every two hours. Thereafter, the solution that remained in the dialysis bag was transferred to a separation funnel and washed with dichloromethane until the dichloromethane layer was colorless. Finally, the water layer was concentrated to yield 13 mL (1.68 mg/mL) Si—[Ru] nanoparticles (Si—[Ru] NPs).

2.2 Characterization of the Si—[Ru] nanoparticles 2.2.1 X-Ray Photoelectron Spectroscopy (XPS)

The Si—[Ru] nanoparticles were characterized by X-ray photoelectron spectroscopy.

The chemical composition of the Si—[Ru] NPs was identified by means of XPS measurements. As shown in FIG. 1(a), the Si—[Ru] nanoparticles contain the following elements: C, N, O, P, Ru, F and Si (cf. Table 1). The bonding energy of Si2p is at 101.53 eV and corresponds to an Si-C bond. No trace of silica formation was observed (~104 eV).

Furthermore, the deconvolution of N scan was performed as shown in FIG. 1(d) and summarized in Table 2. The deconvolution of N scan demonstrates that the Si—[Ru] nanoparticles contain three different types of nitrogen: pyridine N from the ruthenium bipyridine, amine N from the 3-aminopropyl silicon nanoparticles, and amide N from the coupling of amine-terminated 3-amino-propyl silicon nanoparticles and the ruthenium complex, which proves that the ruthenium complex is covalently bound to the 3-aminopropyl silicon nanoparticles.

TABLE 1

XPS data of Si—[Ru] nanoparticles.

|      | Peak, eV | FWHM, eV | Atomic ratio, % |
|------|----------|----------|-----------------|
| C1s  | 284.80   | 2.94     | 63.24           |
| N1s  | 399.46   | 2.93     | 10.93           |
| O1s  | 531.22   | 3.16     | 13.87           |
| P2p  | 136.09   | 1.63     | 1.10            |
| Ru3d5| 280.53   | 2.20     | 0.56            |
| F1s  | 685.74   | 2.88     | 6.36            |
| Si2p | 101.53   | 2.93     | 3.94            |

TABLE 2

XPS data of Si—[Ru] nanoparticles in N scan.

|            | Peak, eV | FWHM, eV | Atomic ratio, % |
|------------|----------|----------|-----------------|
| pyridine N | 398.50   | 1.99     | 48.38           |
| amine N    | 399.41   | 1.34     | 43.619          |
| amide N    | 400.05   | 1.07     | 8.43            |

2.2.2 Transmission Electron Microscopy (TEM) Imaging

FIG. 2 shows TEM images of Si—[Ru] nanoparticles. FIG. 2 demonstrates that the Si—[Ru] nanoparticles have a size of about 4 nm and a crystalline structure.

2.2.3 Dynamic Light Scattering (DLS) and Zeta potential

The results of the dynamic light scattering (DLS) measurements show that the hydrodynamic radius of the Si—[Ru] nanoparticles is about 51.7 nm and that the zeta potential is 27.05 mV.

TABLE 3

Dynamic light scattering and Zeta potential.

| | Si—[Ru] NPs |
|---|---|
| Hydrodynamic radius | 51.7 ± 13.3 nm |
| Zeta potential | 27.05 mV |

2.2.4 Photophysical Properties

In order to compare the Si—[Ru] nanoparticles with standard Rubpy, UV-Vis absorption was performed in order to monitor the absorbance which is necessary to reach the same absorption. Due to the lack of absorption of silicon nanoparticles in the range of 400 to 500 nm, the MLCT absorption band of ruthenium bipyridine can be directly fitted when two absorbances are equal to have the same concentration as the ruthenium complex in Si—[Ru] nanoparticles and in Rubpy.

As shown in FIG. 3(a), Rubpy was measured at $10^{-5}$ M in water solution, the absorption bands at 245, 253 and 286 nm are assigned to the ligand $\pi\pi^*$ transition, the absorption bands at 456 nm is assigned to the MLCT band. The absorbance of Si—[Ru] nanoparticles was tuned to be equal to Rubpy at 456 nm (MLCT band) to reach $10^{-5}$ M. The absorption peaks at 245, 256, 286 and 456 nm are assigned to Rubpy and the increase of absorption intensity below 250 nm is due to the presence of Si nanoparticles.

The emission spectra were recorded at $10^{-5}$ M in aqueous solution and are shown in FIG. 3(b). Both Rubpy and Si—[Ru] nanoparticles exhibit same emission profile, intensity and peak centered at 630 nm. Also, the lifetimes of Rubpy and Si—[Ru] nanoparticles are identical, indicating no emission quenching in the Si—[Ru] nanoparticles. Both Rubpy and Si—[Ru] nanoparticles show the emission quantum yield 3.5%.

Furthermore, to examine the ECL efficiency, the UV-Vis absorption of both compounds was performed in ProCell solution at $10^{-5}$ M as shown in FIG. 4. The photophysical data are summarized in Table 4.

TABLE 4

Photophysical data of Si NPs, Si—[Ru] nanoparticles and Rubpy in water solution.

| H₂O | $\lambda_{Absorption}$, nm | $\lambda_{Emission}$, nm[a] | Lifetime τ, ns[a] | Q.Y.[d] |
|---|---|---|---|---|
| Si—NH2 NPs | — | 451 | 2.94 (68%), 14.04 (32%)[b] | 2.6% |
| Si—[Ru] NPs | 245, 253, 286, 456 | 630 | 1.12[b] 323.8[c] | 3.5% |
| Ru complex | 206, 245, 253, 286, 456 | 630 | 305.8[c] | 3.5% |

[a]$\lambda_{ex}$ = 375 nm,
[b]$\lambda_{em}$ = 451 nm,
[c]$\lambda_{em}$ = 630 nm,
[d]quantum yield measurement was performed using integrating sphere.

2.3 Electrochemiluminescence (ECL Performance)

Figure 5A:
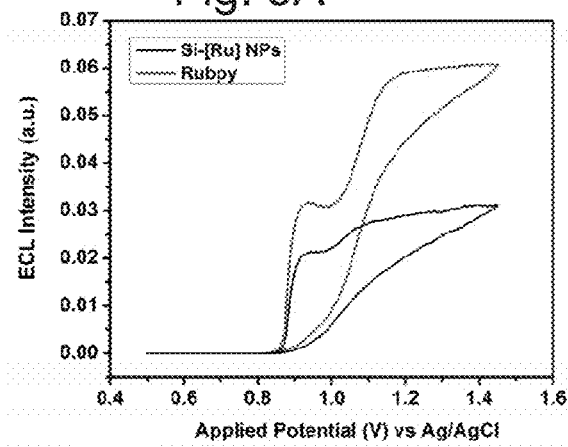
FIG. 5A shows the ECL intensity recorded during a cyclic voltammetry at a scan rate of 0.05 $Vs^{-1}$ of $10^{-5}$ M Rubpy (upper line) and $10^{-5}$ M Si—[Ru] nanoparticles (lower line) in ProCell.
Figure 5B:
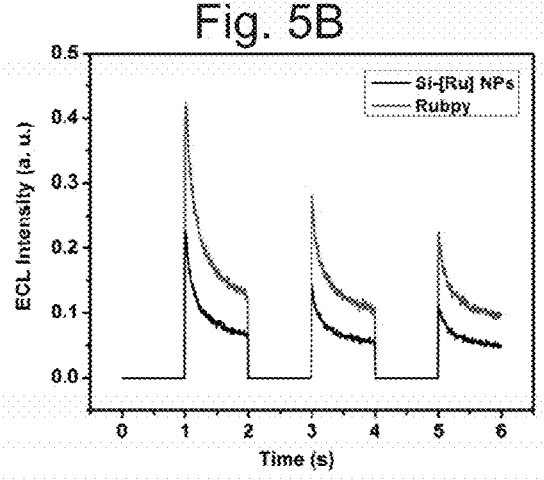
FIG. 5B shows the ECL intensity vs time of $10^{-5}$ M Rubpy (upper line) and $10^{-5}$ M Si—[Ru] nanoparticles (lower line) in ProCell.
Figure 5C:
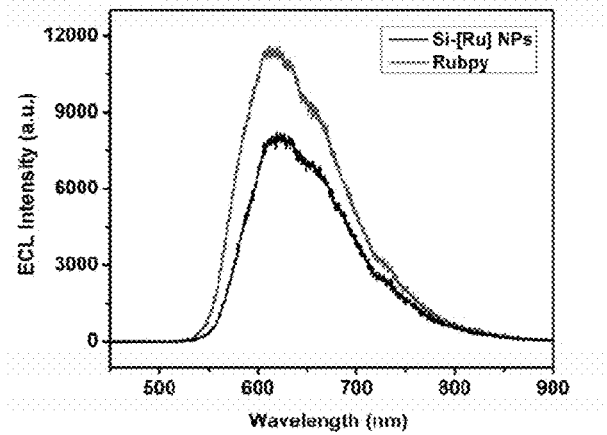
FIG. 5C shows ECL spectra of $10^{-5}$ M Rubpy (upper line) and $10^{-5}$ M Si—[Ru] nanoparticles (lower line) in ProCell.

FIG. 5(c) shows that the ECL emission of Si—[Ru] nanoparticles has a profile, which is identical to the Rubpy standard but has a lower intensity. The ECL efficiency is 70% in comparison to Rubpy (100%). Furthermore, chronoamperometric measurements were performed and calculated for the ECL efficiency. Nine experiments were performed on 3 different days, 3 experiments per day. The error was less than 10%. The ECL efficiency of Si—[Ru] nanoparticles in chronoamperometric measurements is 67% compared to Rubpy (100%). All ECL data are summarized in Table 5.

TABLE 5

ECL data of Si—[Ru] nanoparticles.

| ProCell | Rubpy | Si—[Ru] NPs |
|---|---|---|
| Chronoamperometry | 1.00 | 0.67 |
| ECL emission spectrum | 1.00 | 0.70 |

Rubpy was used as reference (ECL efficiency = 1.00) For chronoamperometric measurements, 9 experiments were performed (3 times per day and 3 different days), the error is less than 10%.

2.4 Calculation of the Diffusion Coefficient

Figure 6A:
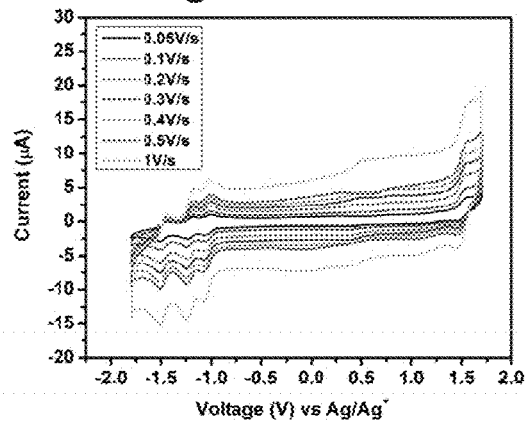
FIG. 6A shows cyclic voltammetries at different scan rates of 0.1 mM Rubpy in 0.1 M $TBAPF_6$ DMF solution, ranging from 0.05 $Vs^{-1}$ to 1 $Vs^{-1}$.
Figure 6B:
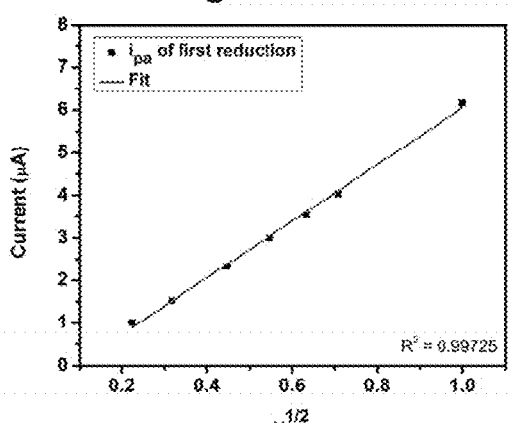
FIG. 6B shows I vs $v^{1/2}$ plot of Rubpy.
Figure 6C:
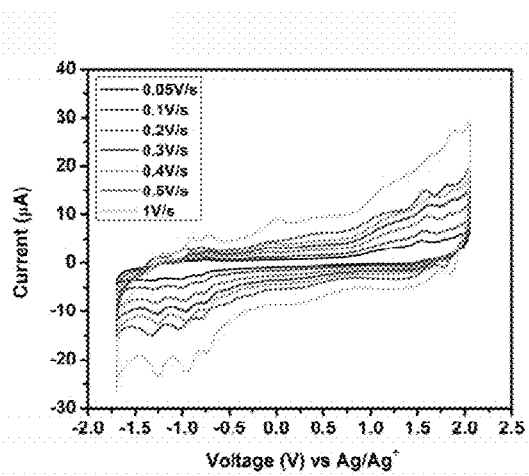
FIG. 6C shows cyclic voltammetries at different scan rates of 0.1 mM Si—[Ru] nanoparticles in 0.1 M $TBAPF_6$ DMF solution, ranging from 0.05 $Vs^{-1}$ to 1 $Vs^{-1}$.
Figure 6D:
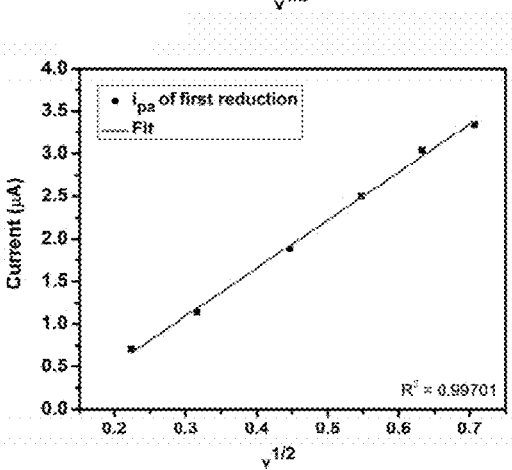
FIG. 6D shows I vs $v^{1/2}$ plot of Si—[Ru] nanoparticles.

In order to study the low ECL efficiency of Si—[Ru] nanoparticles, the diffusion coefficient was calculated by cyclic voltammetry in different scan rates. The results of these cyclic voltammetries are shown in FIGS. 6(a) and 6(c). Further, FIGS. 6(b) and 6(d) show that the current is proportional to the root of scan rate, indicating that the mass transfer behavior is diffusion control and follows Randles-Sevcik equation which allows the calculation of the diffusion coefficient. The results are summarized in Table 6. This lower diffusion coefficient of Si-[Ru] nanoparticles causes lower ECL efficiency in comparison to Rubpy. All data are summarized in Table 6.

TABLE 6

Comparison of ECL efficiency with diffusion coefficient of Rubpy and Si—[Ru] nanoparticles

| ProCell | Rubpy | Si—[Ru] NPs |
|---|---|---|
| Chronoamperometry | 1.00 | 0.67 |
| ECL emission spectrum | 1.00 | 0.70 |
| Diffusion coefficient (cm²/s) | 1.11 × 10⁻⁶ | 9.43 × 10⁻⁷ |

Example 3

Preparation and Characterization of [Ir]-labeled Silicon Nanoparticles and ECL Performance thereof

3.1 Preparation of [Ir]-labeled Silicon Nanoparticles

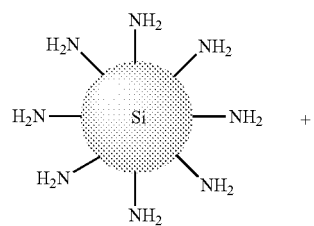

-continued

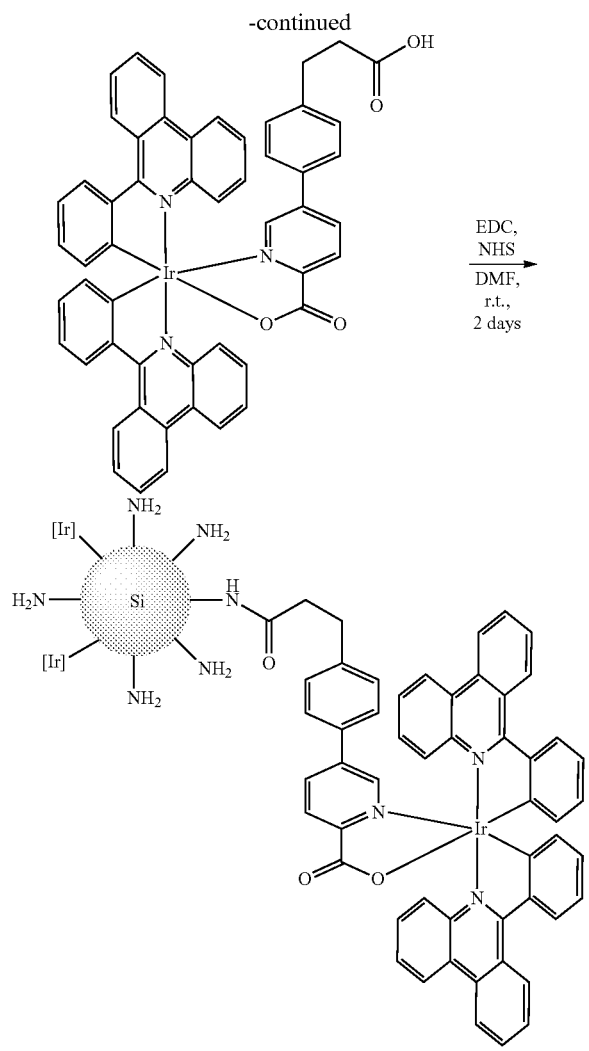

The Ir complex (52.9 mg, 54.5 µmol) (CAS Registry Number 1393128-57-8), EDC (16.9 mg, 0.109 mmol) and NHS (12.5 mg, 0.109 mmol) were dissolved in 7 mL dried DMF in a 25 ml flask, and stirred for 1 hour under Ar atmosphere at room temperature. Thereafter, amine-terminated 3-aminopropyl silicon nanoparticles (1.8 mL in H$_2$O, 40 mg) and diisopropylethylamine (10 µL) were added slowly to the solution, and the reaction was stirred for 2 days under argon atmosphere at room temperature. Then, the solvent was removed under vacuum. The crude product was washed with water and dichloromethane in order to remove unreacted Ir complexes and unreacted amine-terminated 3-aminopropyl silicon nanoparticles. The product was dispersed into 15 mL DMF to yield 4.12 mg/mL Si—[Ir] NPs.

3.2 Characterization of the Si—[Ir] Nanoparticles 3.2.1 X-Ray Photoelectron Spectroscopy (XPS)

The Si—[Ir] NPs were characterized by X-ray photoelectron spectroscopy.

Figure 7A:
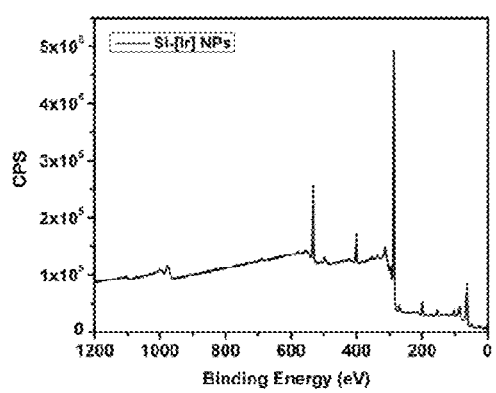
FIG. 7A shows a survey scan of XPS spectra of Si—[Ir] nanoparticles.
Figure 7B:
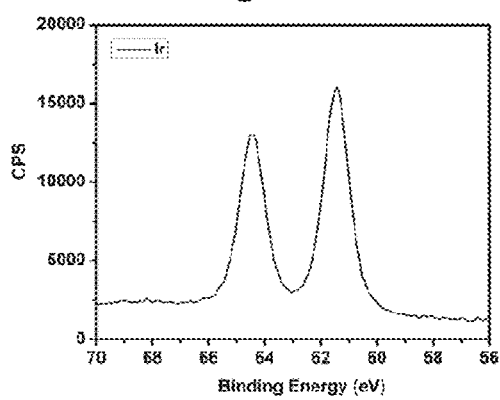
FIG. 7B shows an Ir scan of XPS spectra of Si—[Ir] nanoparticles.
Figure 7C:
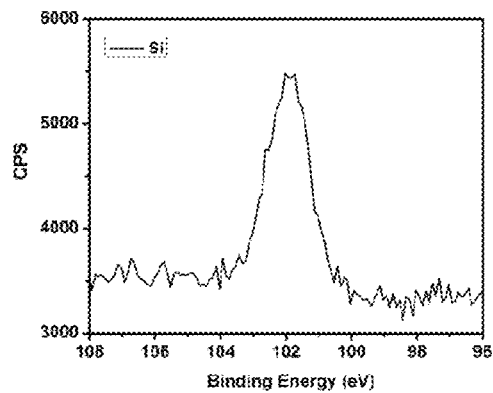
FIG. 7C shows an Si scan of XPS spectra of Si—[Ir] nanoparticles.

The chemical composition of Si—[Ir] NPs was identified by means of XPS measurements. As shown in FIG. 7(a), the Si—[Ir] nanoparticles contain the following elements: C, N, O, Ir and Si (cf. Table 7). The bonding energy of Si2p is at 102.00 eV and corresponds to a Si—C bond. No trace of silica formation (~104 eV) was identified.

Figure 7D:
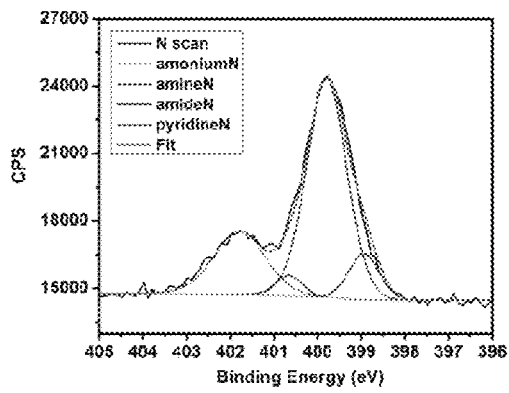
FIG. 7D shows an N scan with deconvolution of XPS spectra of Si—[Ir] nanoparticles.

Furthermore, the deconvolution of N scan was performed as shown in FIG. 7(d) and summarized in Table 7. The deconvolution of N scan shows that the Si—[Ir] nanoparticles contain four different types of nitrogen: pyridine nitrogen from Rubpy, amine N and ammonium N from the amine-terminated 3-aminopropyl silicon nanoparticles and amid N from the coupling of amine-terminated 3-aminopropyl silicon nanoparticles with the iridum complex, which proves that the iridium complex is covalently bound to the silicon nanoparticles.

TABLE 7

XPS data of Si—[Ir] nanoparticles.

| | Peak, eV | FWHM, eV | Atomic ratio, % |
|---|---|---|---|
| C1s | 284.80 | 2.79 | 76.47 |
| O1s | 531.84 | 3.07 | 11.17 |
| N1s | 399.97 | 3.18 | 7.30 |
| Si2p | 102.00 | 2.63 | 1.96 |
| Ir4f | 62.06 | 2.85 | 1.12 |

TABLE 8

XPS data of Si—[Ir] nanoparticles in N scan.

| | Peak, eV | FWHM, eV | Atomic ratio, % |
|---|---|---|---|
| pyridineN | 398.94 | 0.81 | 10.14 |
| amineN | 399.79 | 1.07 | 62.9 |
| amideN | 400.66 | 0.69 | 3.73 |
| ammoniumN | 401.79 | 1.37 | 23.23 |

3.2.2 Transmission Electron Microscopy (TEM) Imgaging

FIG. 8 shows a TEM image of Si—[Ir] nanoparticles. FIG. 8 demonstrates that the Si—[Ir] nanoparticles have a size of about 4 nm and a crystalline structure.

3.2.3 Photophysical Properties

In order to compare the Si—[Ir] nanoparticles with the Ir complex, the UV-Vis absorption was performed in order to monitor the absorbance, which is necessary to reach same absorption than the Ir complex. Due to the lack of absorption of Si NPs in the range of 400 to 500 nm, the MLCT absorption band of the Ir complex can be directly fitted when two absorbances are equal, to have the same concentration as the Ir complex in Si—[Ir] NPs and in the Ir complex.

Figure 9:
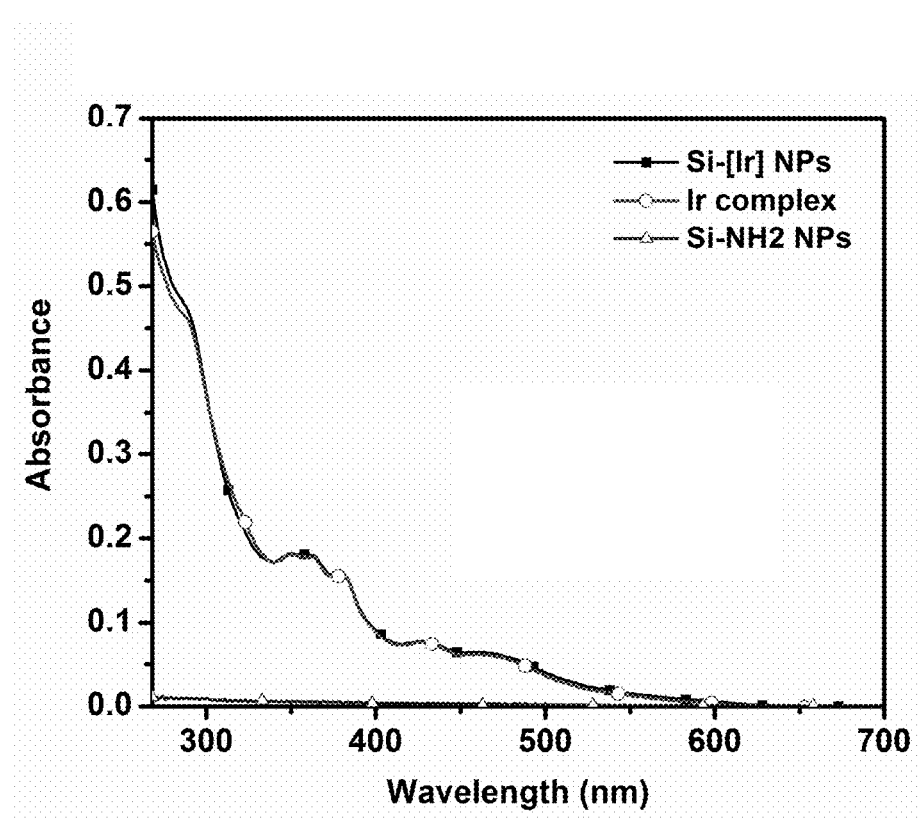
FIG. 9 shows UV-Vis absorption spectra of Si—$NH_2$ NPs, Si—[Ir] NPs and Ir complex in DMF solution.

As shown in FIG. 9, Ir complex was measured at $10^{-5}$ M in DMF solution, absorption bands at 288, 350, 358 and 380 nm are assigned to the ligand $\pi\pi^*$ transition, the absorption bands at 430 and 468 nm are assigned to the MLCT band. The absorbance of Si—[Ir] NPs was tuned to be equal to Ir complex at MLCT band to reach $10^{-5}$ M. The absorption peaks at 288, 350, 358, 430 and 468 nm are assigned to the Ir complex.

Figure 10:
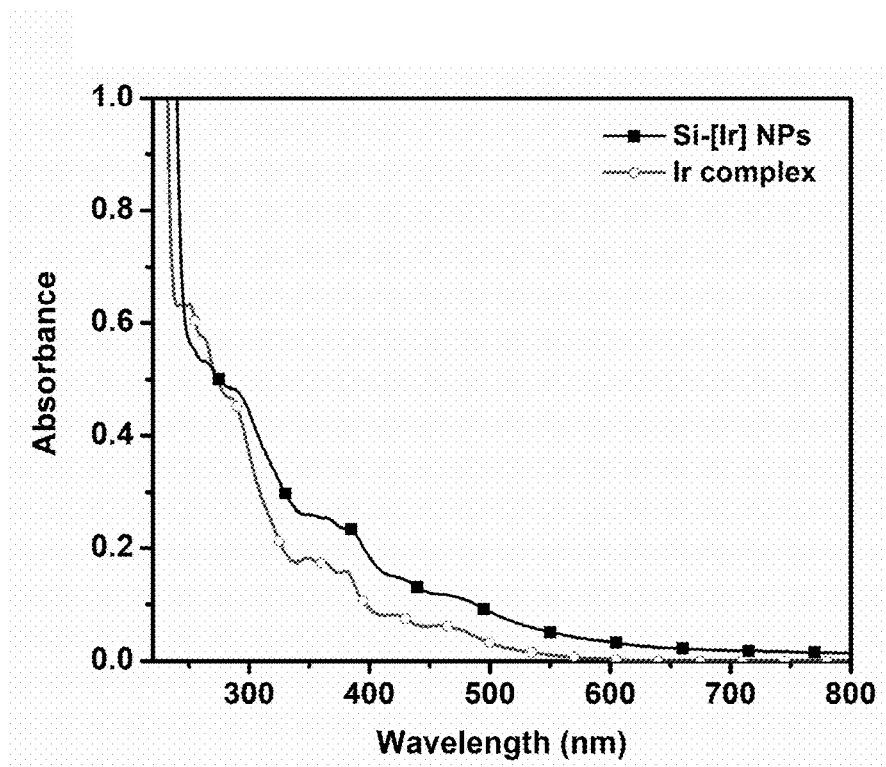
FIG. 10 shows UV-Vis absorption spectra of Si—[Ir] NPs and Ir complex in ProCell solution.

Furthermore, to examine the ECL efficiency, the UV-Vis absorption of both compounds was performed in ProCell solution at $10^{-5}$ M as shown in FIG. 10.

3.3 Electrochemiluminescence (ECL) Performance

Figure 11A:
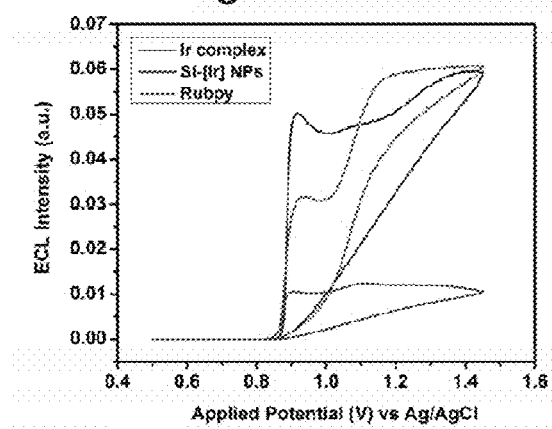
FIG. 11A shows ECL intensity recorded during a cyclic voltammetry at scan rate 0.05 $Vs^{-1}$ of $10^{-5}$ M Rubpy (upper line), $10^{-5}$ M Ir complex (lower line) and $10^{-5}$ M Si—[Ir] NPs (middle line) in ProCell.
Figure 11B:
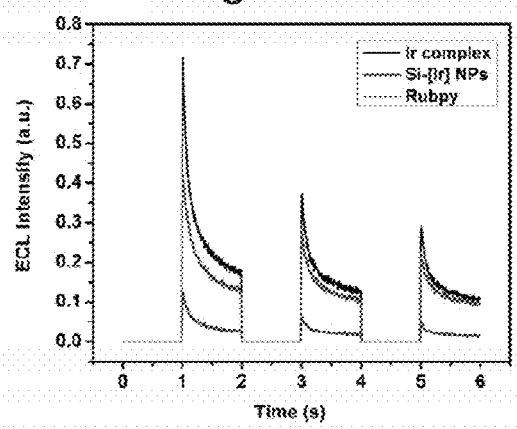
FIG. 11B shows ECL intensity vs time of $10^{-5}$ M Rubpy (upper line), $10^{-5}$ M Ir complex (lower line) and $10^{-5}$ M Si—[Ir] nanoparticles (middle line) in ProCell.
Figure 11C:
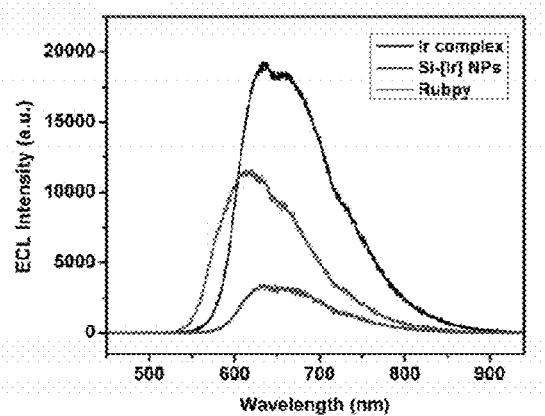
FIG. 11C shows ECL spectra of $10^{-5}$ M Rubpy (upper line), $10^{-5}$ M Ir complex (lower line) and $10^{-5}$ M Si—[Ir] nanoparticles (middle line) in ProCell.

FIG. 11(c) shows that the ECL emission of Si—[Ir] NPs has a profile, which is identical to the Ir complex but has a lower intensity. The ECL efficiency is 28% compared to Rubpy (100%). Also chronoamperometric measurements were performed and calculated for the ECL efficiency. Nine experiments were performed in 3 different days, 3 experiments per day. The error was less than 10%. The ECL efficiency of Si—[Ir] NPs in chronoamperometric measurements is 31% compared to Rubpy (100%). All ECL data are summarized in Table 9.

TABLE 9

| ECL data of Si—[Ir] NPs. | | | |
|---|---|---|---|
| ProCell | Rubpy | Ir | Si—[Ir] NPs |
| Chronoamperometry | 1.00 | 1.32 | 0.31 |
| ECL emission spectrum | 1.00 | 1.77 | 0.28 |

Rubpy was used as reference (ECL efficiency = 1.00) For chronoamperometry method, 9 experiments were performed (3 times per day and 3 different days), the error is less than 10%.

3.4 Calculation of the Diffusion Coefficient

Since the ECL is generated only on the electrode surface, it is import that the mass diffusion rate of analyte to the electrode surface. To study the lower ECL efficiency of the Si—[Ir] NPs, the diffusion coefficient was calculated by cyclic voltammetry in different scan rates as shown in FIG. 12(a).

Figure 12B:
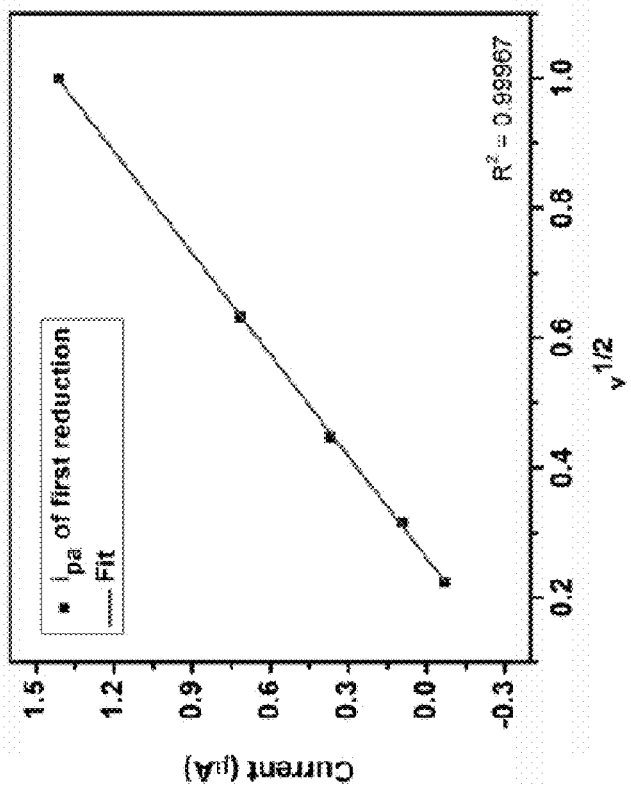
FIG. 12B shows I vs $v^{1/2}$ plot of Si—[Ir] nanoparticles.
Figure 12A:
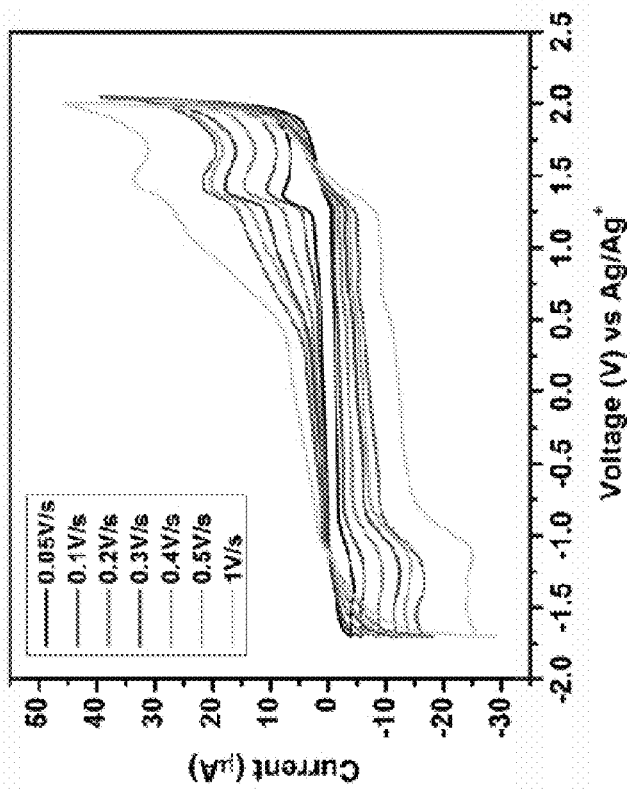
FIG. 12A shows cyclic voltammetries at different scan rates of 0.1 mM Si—[Ir] nanoparticles in 0.1 M $TBAPF_6$ DMF solution, ranging from 0.05 V $s^{-1}$ to 1 $Vs^{-1}$.

In FIG. 12(b), the current is proportional to the root of scan rate, indicating the mass transfer behavior is diffusion control and follows Randles-Sevcik equation which allows the calculation of the diffusion coefficient and is summarized in Table 10. The lower ECL efficiency of Si—[Ir] NPs is due to the slower diffusion coefficient of $3.21 \times 10^{-7}$ $cm^2 s^{-1}$ under homogenous conditions All data are summarized in Table 10.

TABLE 10

| Comparison of ECL efficiency with diffusion coefficient of Rubpy and Si—[Ir] NPs. | | |
|---|---|---|
| ProCell | Rubpy | Si—[Ir] NPs |
| Chronoamperometry | 1.00 | 0.31 |
| ECL emission spectrum | 1.00 | 0.28 |
| Diffusion coefficient ($cm^2/s$) | $1.11 \times 10^{-6}$ | $3.21 \times 10^{-7}$ |

Example 4

Functionalization of [Ru]-Labeled Silicon Nanoparticles 4.1 Reaction of a Heterobifunctional Linker with [Ru]-Labeled Silicon Nanoparticles

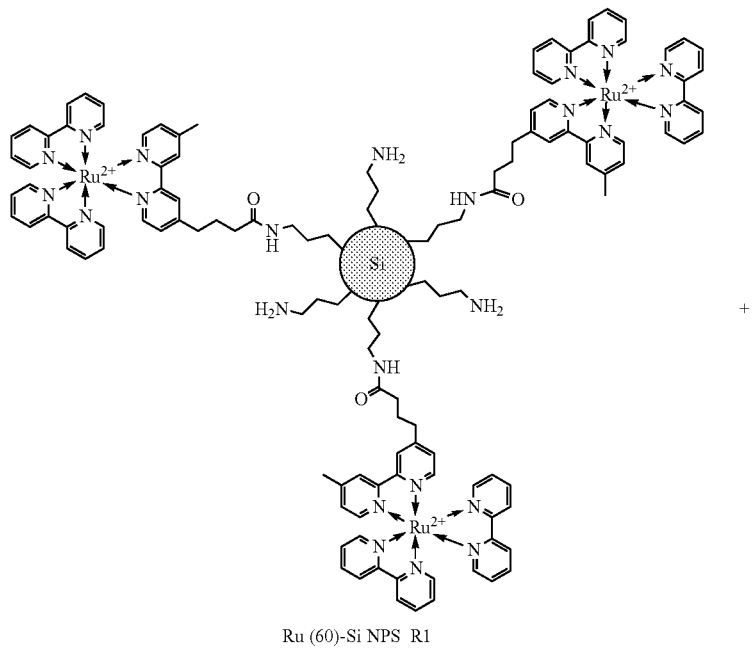

Ru (60)-Si NPS R1

+

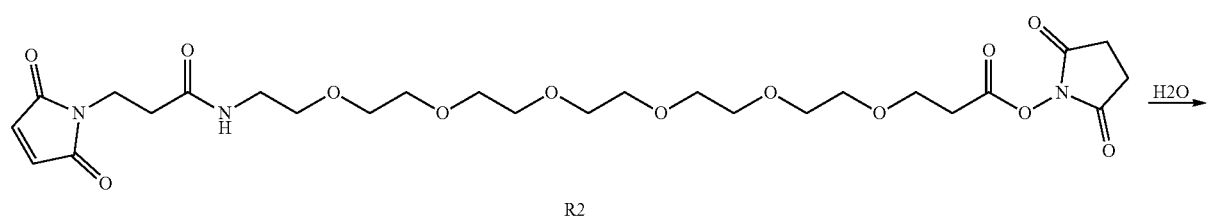

R2

-continued

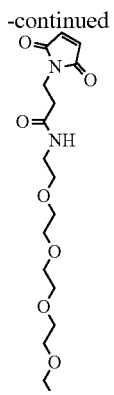

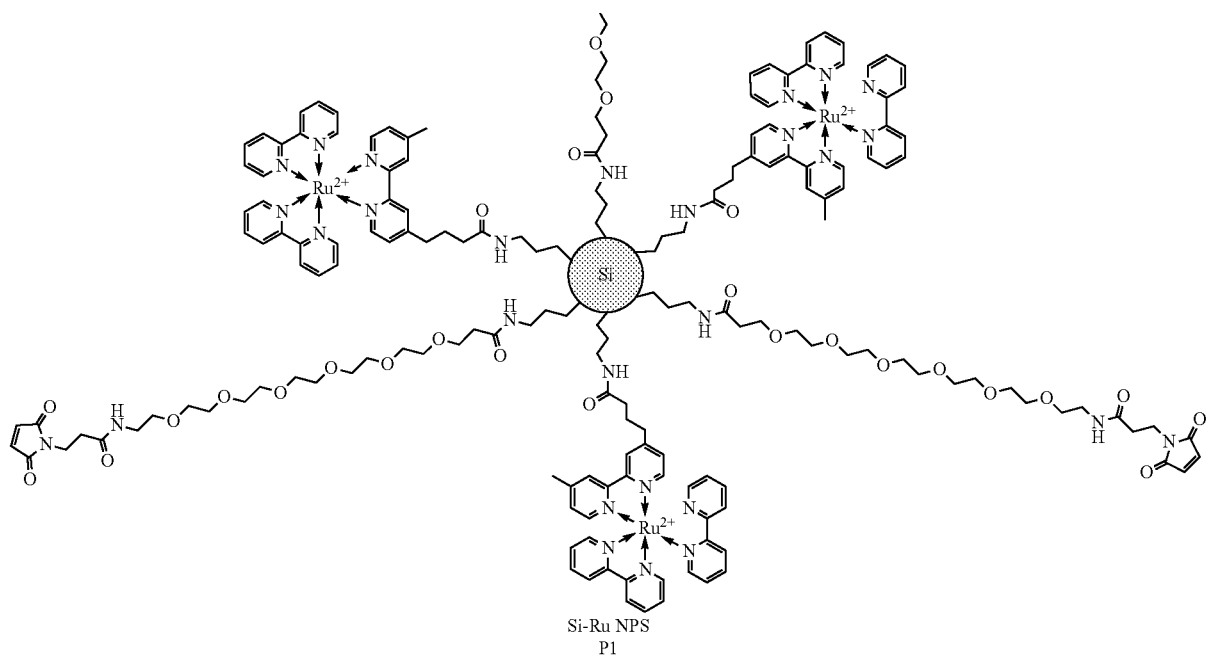

Si-Ru NPS
P1

Si—NP functionalized with 60 ruthenium complexes (R1) (1.68 mg in 1 mL solution) and 3-[2-(2-{2-[2-(2-{2-[3-(2,5-Dioxo-2,5-dihydro-pyrrol-1-yl)-propionylamino]-ethoxy}-ethoxy)-ethoxy]-ethoxy}-ethoxy)-ethoxy]-propionic acid 2,5-dioxo-pyrrolidin-1-yl ester (R2) were mixed in a 10 mL flask. The reaction was stirred at room temperature overnight. Then, the red solution was purified by dialysis using a 1 kDa membrane to remove the excess of R2. After 2 days of dialysis, the red solution was lyophilized to give a red solid. The red solid was re-suspended in 2 mL of water and the supension was filtered to remove the non-soluble residue.

Yield: 2 mL final solution: orange solution

Average concentration of Ru in solution by UV ($\lambda_{max}$: 456; ε: 14600): 0.52 Conc.: 3.5 $10^{-05}$ M of Ru complex 4.2 Conjugation of [Ru]-Labeled Silicon Nanoparticles Functionalized with a Heterobifunctional Linker with an Antibody The conjugation procedure was carried out as described in U.S. Pat. No. 7,521,541. Maleimide functionalized Si-nanoparticles functionalized with Ruthenium complexes were conjugated with Fab-fragments from MAb<TN-T>Chim-5D8-IgG via site-specific conjugation using engineered cysteins (ThioMab technology) and purified via gel filtration (Superdex 200).

4.3 Reaction of a Modified Analyte with [Ru]-Labeled Silicon Nanoparticles
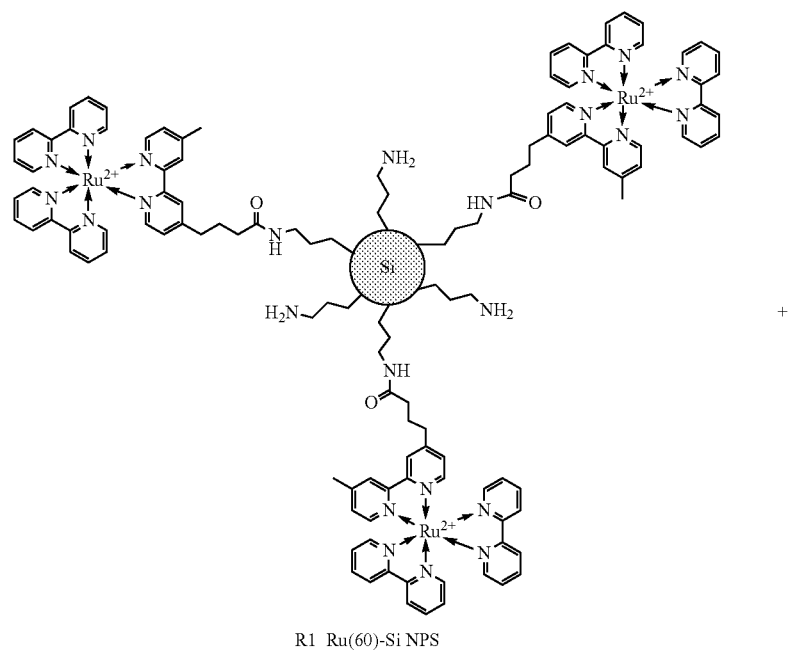
R1 Ru(60)-Si NPS
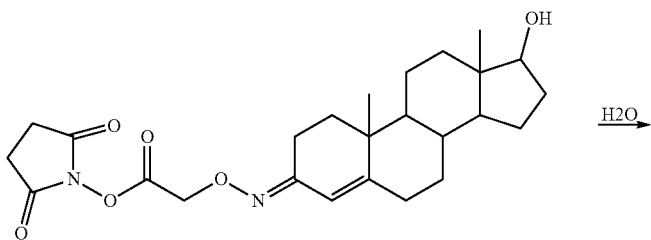
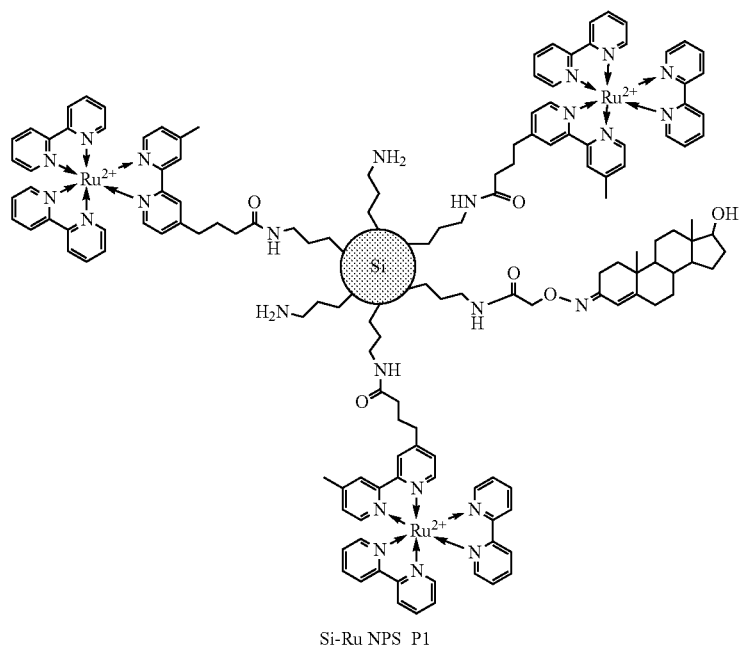
Si-Ru NPS P1

Si—NP functionalized with 60 ruthenium complexes (R1) (1.68 mg in 1 mL solution) and testosterone-3-carboxymethyloxim-NHS ester were mixed in a 10 mL flask. The mixture was stirred at room temperature overnight. Then, the red solution was purified by dialysis using a 1 kDa membrane to remove the excess of R2. After 2 days of dialysis, the red solution was lyophilized to give a red solid. The red solid was re-suspended in 2 mL of water and the suspension was filtered to remove the non-soluble residue.

The invention claimed is:

1. Multifunctionalized silicon nanoparticles comprising
   (a) a silicon core of a size of from 1 nm to 10 nm,
   (b) amine-terminated $C_3$-$C_{18}$ aminoalkyl groups, amine-terminated 3-(2-amino-ethoxy)-propyl groups, amine-terminated 3-[2-(2-amino-ethoxy)-ethoxyl]-propyl groups or amine-terminated 2-(4-amino-methyl-phenyl)-ethyl groups, wherein the groups are covalently bound to the silicon core,
   (c) from 1 to 10 affinity binding agents covalently bound to amine-terminated $C_3$-$C_{18}$ aminoalkyl groups, to amine-terminated 3-(2-amino-ethoxy)-propyl groups, to amine-terminated 3-[2-(2-amino-ethoxy)-ethoxyl]-propyl groups or to amine-terminated 2-(4-amino-methyl-phenyl)-ethyl groups, via a linker, wherein the affinity binding agent is a steroid, and
   (d) from 1 to 100 electrochemiluminescent compounds covalently bound to amine-terminated $C_3$-$C_{18}$ aminoalkyl groups, to amine-terminated 3-(2-amino-ethoxy)-propyl groups, to amine-terminated 3-[2-(2-amino-ethoxy)-ethoxyl]-propyl groups or to amine-terminated 2-(4-amino-methyl-phenyl)-ethyl groups, via a linker.

2. The multifunctional silicon nanoparticles according to claim 1 corresponding to Formula (I)

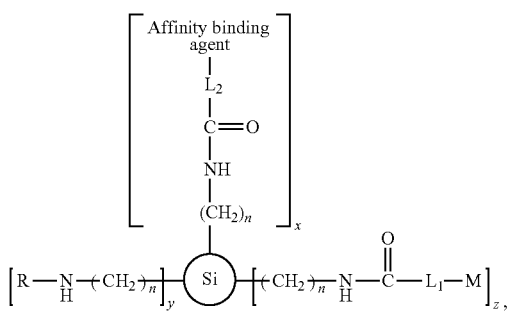

where n is an integer from 3 to 18, x is an integer from 1 to 10, y is at least 1, z is an integer from 1 to 100, $L_1$ is a linker, $L_2$ is a linker, wherein $L_1$ and $L_2$ are identical or different, Si is a silicon core having a size of from 1 nm to 10 nm, R is H, —CO-$L_2$ with one reactive group, —CO-deactivated $L_2$, wherein $L_2$ is as defined above, or a residue of a surface modification reagent, and M is an electrochemiluminescent metal complex, or a salt thereof.

3. The multifunctionalized silicon nanoparticles according to claim 1, wherein the affinity binding agent is a partner or member of an affinity binding pair.

4. The multifunctionalized silicon nanoparticles according to claim 1, wherein the affinity binding agent is a member of a binding pair selected from antigen and antibody.

5. The multifunctionalized silicon nanoparticles according to claim 2, wherein n is 3, 6 or 11.

6. The multifunctionalized silicon nanoparticles according to claim 2, wherein x is an integer from 1 to 5.

7. The multifunctionalized silicon nanoparticles according to claim 2, wherein y is an integer from 1 to 1000.

8. The multifunctionalized silicon nanoparticles according to claim 2, wherein $L_1$ has as a backbone a straight or branched unsubstituted or substituted $C_1$-$C_{20}$ alkyl chain, $C_1$-$C_{20}$ alkenyl chain, or a 1 to 20 atom chain consisting of carbon atoms, substituted carbon atoms and/or one or more atoms selected from O, N and S, or a chain as described before with the backbone containing one or more cyclic or heterocyclic aromatic or non-aromatic ring systems.

9. The multifunctionalized silicon nanoparticles according to claim 2, wherein $_2$ is a heterobifunctional crosslinker.

10. The multifunctionalized silicon nanoparticles according to claim 9, wherein the heterobifunctional crosslinker binds sulfhydryl groups and amino groups.

11. The multifunctionalized nanoparticles of claim 1, wherein the steroid is selected from the group consisting of estradiol, estrone, progesterone, 17-hydroxyprogestrone, cortisol, testosterone, androstendione, and a vitamin D.

12. The multifunctional silicone nanoparticles of claim 1, wherein the electrochemiluminescent compound is an electrochemiluminescent ruthenium complex.

* * * * *